United States Patent
Roma et al.

(10) Patent No.: US 11,390,854 B2
(45) Date of Patent: Jul. 19, 2022

(54) HUMAN PORPHOBILINOGEN DEAMINASE DERIVED PROTEINS AND POLYNUCLEOTIDES AND USES THEREOF

(71) Applicant: FUNDACION PARA LA INVESTIGACION MEDICA APLICADA, Pamplona (ES)

(72) Inventors: Antonio Fontanellas Roma, Pamplona (ES); Irantzu Serrano Mendioroz, Pamplona (ES); Pedro Berraondo Lopez, Pamplona (ES)

(73) Assignee: Fundacion Para la Investigacion Medica Aplicada, Pamplona (ES)

( * ) Notice: Subject to any disclaimer, the term of this patent is extended or adjusted under 35 U.S.C. 154(b) by 132 days.

(21) Appl. No.: 16/611,688

(22) PCT Filed: May 18, 2017

(86) PCT No.: PCT/EP2017/061944
§ 371 (c)(1),
(2) Date: Nov. 7, 2019

(87) PCT Pub. No.: WO2018/206125
PCT Pub. Date: Nov. 15, 2018

(65) Prior Publication Data
US 2021/0139866 A1 May 13, 2021

(30) Foreign Application Priority Data
May 9, 2017 (EP) ..................................... 17382257

(51) Int. Cl.
*C12N 9/10* (2006.01)
*C07K 14/775* (2006.01)
*A61K 38/00* (2006.01)

(52) U.S. Cl.
CPC .......... *C12N 9/1085* (2013.01); *C07K 14/775* (2013.01); *C12Y 205/01061* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 8,697,665 B2 | 4/2014 | Fontanellas Romá et al. | |
| 2014/0206752 A1 | 7/2014 | Afeyan et al. | |
| 2015/0086614 A1 | 3/2015 | Bancel et al. | |
| 2016/0074475 A1 | 3/2016 | Prieto Valtueña et al. | |
| 2016/0304552 A1 | 10/2016 | Roy et al. | |
| 2020/0085916 A1* | 3/2020 | Martini ..................... | A61P 7/08 |

FOREIGN PATENT DOCUMENTS

| | | |
|---|---|---|
| EP | 2305309 A2 | 4/2011 |
| EP | 2918275 B1 | 5/2016 |
| WO | WO 99/37325 A2 | 7/1999 |
| WO | WO 2009/150284 A2 | 12/2009 |
| WO | WO 2010/036118 A1 | 4/2010 |
| WO | WO 2016/011226 A1 | 1/2016 |
| WO | WO 2016/011306 A2 | 1/2016 |
| WO | WO 2016/014846 A1 | 1/2016 |
| WO | WO 2016/037931 A1 | 3/2016 |
| WO | WO 2016/097218 A1 | 6/2016 |
| WO | WO 2016/097219 A1 | 6/2016 |

OTHER PUBLICATIONS

Altschul, S. et al., "Basic Local Alignment Search Tool," J. Mol. Biol., 1990, 215:403-410.
Anderson and Desnick, "Purification and Properties of Uroporphyrinogen I Synthase from Human Erythrocytes," J Biol Chem. 1980; 255(5):1993-1999.
anderson , K. et al., "Recommendations for the Diagnosis and Treatment of the Acute Porphyrias," Ann Intern Med. 2005;142(6):439-450.
Berraondo, P. et al., "IFN-α Gene Therapy for Woodchuck Hepatitis with Adeno-associated Virus: Differences in Duration of Gene Expression and Antiviral Activity Using Intraportal or Intramuscular Routes," Mol. Ther., Jul. 2005; 12(1): 68-76.
Biospace, "uniQure Release: AIPGENE Consortium Presents 1 Year Follow-Up Clinical Data From Acute Intermittent Porphyria Phase I Clinical Trial Using AAV5-PBGD Gene Therapy Candidate," Oct. 27, 2014, 7 pages, retrieved from www.biospace.com/article/releases/uniqure-release-b-aipgene-consortium-b-presents-1-year-follow-up-clinical-data-from-acute-intermittent-porphyria-phase-i-clinical-trial-using-aav5/.
Blum, C. et al., "High Density Lipoprotein Metabolism in Man," J. Clin. Invest., Oct. 1977, 60:795-807.
Büning, H et al., "Recent developments in adeno-associated virus vector technology," J Gene Med 2008; 10:717-733.
ClinicalTrials.gov Identifier: NCT02082860, Phase I Gene Therapy Clinical Trial Using the Vector rAAV2/5-PBGD for the Treatment of Acute Intermittent Porphyria, First Posted—Mar. 10, 2014, Last Update Posted—Dec. 18, 2014, retrieved from clinicaltrials.gov/ct2/show/NCT02082860, 9 pages.
D'Avola, D. et al., "Phase I open label liver-directed gene therapy clinical trial for acute intermittent porphyria," J Hepatol. 2016, 65:776-783.
Digna Biotech, Pipeline: Clinical Products, Apr. 4, 2016, 1 page, retrieved from web.archive.org/web/20160404231436/http://dignabiotech.com/r_d.Pipeline.asp.
Durocher, Y. et al., "High-level and high-throughput recombinant protein production by transient transfection of suspension-growing human 293-EBNA1 cells," Nucleic Acids Research, 2002, 30(2):E9, 9 pages.

(Continued)

*Primary Examiner* — Anand U Desai
(74) *Attorney, Agent, or Firm* — Cooley LLP; Heidi A. Erlacher; Matthew Pavao

(57) ABSTRACT

The present disclosure relates to human porphobilinogen deaminase derived proteins and polynucleotides and methods of using these proteins and polynucleotides.

31 Claims, 9 Drawing Sheets
Specification includes a Sequence Listing.

(56) References Cited

OTHER PUBLICATIONS

Eisenberg, S. et al., "Metabolic fate of rat and human lipoprotein apoproteins in the rat," J. Lipid Res., 1973, 14:446-458.
Fontanellas, A., et al., "Emerging therapies for acute intermittent porphyria," Expert Rev Mol Med. Nov. 2, 2016;18:e17, 13 pages.
Fontanellas, A., et al., "Intensive Pharmacological Immunosuppression Allows for Repetitive Liver Gene Transfer With Recombinant Adenovirus in Nonhuman Primates," Molecular Therapy, Apr. 2010, vol. 18, No. 4, pp. 754-765.
GenBank Accession No. KT235804.1, Adeno-assoociated virus isolate Anc80L65 capsid protein (VP1) gene, complete cds, Aug. 7, 2015, 2 pages.
Graversen, J. et al., "Trimerization of Apolipoprotein A-I Retards Plasma Clearance and Preserves Antiatherosclerotic Properties," J Cardiovasc Pharmacol., 2008, 51:170-177.
Hagenbaugh, A. et al., "Altered Immune Responses in Interleukin 10 Transgenic Mice," J Exp Med, Jun. 1997, 185(12): 2101-2110.
Henikoff and Henikoff, "Amino acid substitution matrices from protein blocks," PNAS, 1992, 89, 10915-10919.
Johansson, A. et al., "Correction of the biochemical defect in porphobilinogen deaminase deficient cells by non-viral gene delivery," Molecular and Cellular Biochemistry, 2003, 250: 65-71.
Kauppinen, R. "Porphyrias," Lancet, Jan. 2005, vol. 365, Issue 6455, pp. 241-252.
Kitajima, K. et al., "Persistent liver expression of murine apoA-I using vectors based on adeno-associated viral vectors serotypes 5 and 1," Atherosclerosis, 2006, 186:65-73.
Lindberg, R., et al., "Porphobilinogen deaminase deficiency in mice causes a neuropathy resembling that of human hepatic porphyria," Nature Genetics, 1996, 12:195-199.
Maxwell, F. et al., "Improved production of recombinant AAV by transient transfection of NB324K cells using electroporation," J. Virol. Methods, 1997, 63:129-136.
Monaco, L. et al., "A recombinant apoA-1—protein A hybrid reproduces the binding parameters of HDL to its receptor," The EMBO Journal, 1987, 6(11):3253-3260.
Nathwani, A. et al., "Safe and efficient transduction of the liver after peripheral vein infusion of self-complementary AAV vector results in stable therapeutic expression of human FIX in nonhuman primates," Blood, Feb. 2007, 109(4):1414-1421.
Pañeda, A. et al., "Safety and Liver Transduction Efficacy of rAAV5-cohPBGD in Nonhuman Primates: A Potential Therapy for Acute Intermittent Porphyria," Human Gene Therapy, Dec. 2013, vol. 24, No. 12, pp. 1007-1017.
Parr, M. et al., "Tumor-selective transgene expression in vivo mediated by an E2F-responsive adenoviral vector," Nature Medicine, 1997, 3:1145-1149.
Sardh, E. et al., "Safety, pharmacokinetics and pharmacodynamics of recombinant human porphobilinogen deaminase in healthy subjects and asymptomatic carriers of the acute intermittent porphyria gene who have increased porphyrin precursor excretion," Clin Pharmacokinet. 2007; 46(4):335-349.
UniProtKB—P08397 (HEM3_HUMAN), Aug. 1, 1988, 26 pages.
UniProtKB—Q00623 (APOA1_MOUSE), Apr. 1, 1993, 15 pages.
Unzu, C. et al., "Helper-dependent adenovirus achieve more efficient and persistent liver transgene expression in non-human primates under immunosuppression," Gene Therapy (2015) 22, 856-865.
Unzu, C. et al., "Porphobilinogen deaminase over-expression in hepatocytes, but not in erythrocytes, prevents accumulation of toxic porphyrin precursors in a mouse model of acute intermittent porphyria," Journal of Hepatology, 2010, 52(3):417-424.
Unzu, C. et al., "Sustained Enzymatic Correction by rAAV-Mediated Liver Gene Therapy Protects Against Induced Motor Neuropathy in Acute Porphyria Mice," Mol Ther. 2011; 19(2):243-250.
Unzu, C. et al., "Transient and intensive pharmacological immunosuppression fails to improve AAV-based liver gene transfer in non-human primates," Journal of Translational Medicine 2012, 10:122, 11 pages.
Wright and Lim, "Simultaneous determination of hydroxymethylbilane synthase and uroporphyrinogen III synthase in erythrocytes by high-performance liquid chromatography," Biochem. J., 1983, 213: 85-88.
Zinn, E. et al., "In Silico Reconstruction of the Viral Evolutionary Lineage Yields a Potent Gene Therapy Vector," Cell Reports, Aug. 2015; 12:1056-1068.

\* cited by examiner

SEQUENCE LISTING

```
<160> NUMBER OF SEQ ID NOS: 19

<210> SEQ ID NO 1
<211> LENGTH: 1089
<212> TYPE: DNA
<213> ORGANISM: Artificial Sequence
<220> FEATURE:
<223> OTHER INFORMATION: Codon optimized sequence coding for human
      housekeeping PBGD
<220> FEATURE:
<221> NAME/KEY: CDS
<222> LOCATION: 1..1083
<223> OTHER INFORMATION: /codon_start="1"
      /transl_table=1

<400> SEQUENCE: 1 atg agc ggc aac ggc aac gcc gca gcc acc gcc gag gaa aac agc ccc        48
Met Ser Gly Asn Gly Asn Ala Ala Ala Thr Ala Glu Glu Asn Ser Pro
1               5                   10                  15 aag atg cgg gtg atc aga gtg ggc acc cgg aag agc cag ctg gcc cgg        96
Lys Met Arg Val Ile Arg Val Gly Thr Arg Lys Ser Gln Leu Ala Arg
            20                  25                  30 atc cag acc gac agc gtg gtg gcc acc ctg aag gcc tcc tac ccc ggc       144
Ile Gln Thr Asp Ser Val Val Ala Thr Leu Lys Ala Ser Tyr Pro Gly
        35                  40                  45 ctg cag ttc gag atc att gcc atg agc acc acc ggc gac aag atc ctg       192
Leu Gln Phe Glu Ile Ile Ala Met Ser Thr Thr Gly Asp Lys Ile Leu
    50                  55                  60 gac acc gcc ctg agc aag atc ggc gag aag agc ctg ttc aca aaa gag       240
Asp Thr Ala Leu Ser Lys Ile Gly Glu Lys Ser Leu Phe Thr Lys Glu
65                  70                  75                  80 ctg gaa cac gcc ctg gaa aag aac gag gtg gac ctg gtg gtg cac agc       288
Leu Glu His Ala Leu Glu Lys Asn Glu Val Asp Leu Val Val His Ser
                85                  90                  95 ctg aag gac ctg ccc acc gtg ctg ccc cct ggc ttc acc atc ggc gcc       336
Leu Lys Asp Leu Pro Thr Val Leu Pro Pro Gly Phe Thr Ile Gly Ala
            100                 105                 110 atc tgc aag aga gag aac ccc cac gac gcc gtg gtg ttc cac cct aag       384
```

```
Ile Cys Lys Arg Glu Asn Pro His Asp Ala Val Val Phe His Pro Lys
            115                 120                 125 ttc gtg ggc aag aca ctg gaa acc ctg ccc gag aag tcc gtg gtg ggc      432
Phe Val Gly Lys Thr Leu Glu Thr Leu Pro Glu Lys Ser Val Val Gly
    130                 135                 140 acc agc agc ctg cgg aga gcc gcc cag ctg cag cgg aag ttc ccc cac      480
Thr Ser Ser Leu Arg Arg Ala Ala Gln Leu Gln Arg Lys Phe Pro His
145                 150                 155                 160 ctg gaa ttt cgg agc atc cgg ggc aac ctg aac acc cgg ctg cgg aag      528
Leu Glu Phe Arg Ser Ile Arg Gly Asn Leu Asn Thr Arg Leu Arg Lys
                165                 170                 175 ctg gac gag cag cag gaa ttt tcc gct atc atc ctg gcc aca gcc gga      576
Leu Asp Glu Gln Gln Glu Phe Ser Ala Ile Ile Leu Ala Thr Ala Gly
            180                 185                 190 ctg cag cgg atg ggc tgg cac aac aga gtg ggc cag atc ctg cac ccc      624
Leu Gln Arg Met Gly Trp His Asn Arg Val Gly Gln Ile Leu His Pro
        195                 200                 205 gag gaa tgc atg tac gcc gtg ggc cag gga gcc ctg ggc gtg gaa gtg      672
Glu Glu Cys Met Tyr Ala Val Gly Gln Gly Ala Leu Gly Val Glu Val
    210                 215                 220 cgg gcc aag gac cag gac atc ctg gat ctg gtg ggc gtg ctg cat gac      720
Arg Ala Lys Asp Gln Asp Ile Leu Asp Leu Val Gly Val Leu His Asp
225                 230                 235                 240 ccc gag aca ctg ctg cgg tgt atc gcc gag cgg gcc ttc ctg cgg cac      768
Pro Glu Thr Leu Leu Arg Cys Ile Ala Glu Arg Ala Phe Leu Arg His
                245                 250                 255 ctg gaa ggc ggc tgc agc gtg ccc gtg gcc gtg cac acc gcc atg aag      816
Leu Glu Gly Gly Cys Ser Val Pro Val Ala Val His Thr Ala Met Lys
            260                 265                 270 gac gga cag ctg tac ctg aca ggc ggc gtg tgg agc ctg gac ggc agc      864
Asp Gly Gln Leu Tyr Leu Thr Gly Gly Val Trp Ser Leu Asp Gly Ser
        275                 280                 285 gac agc atc cag gag acc atg cag gcc acc atc cac gtg ccc gcc cag      912
Asp Ser Ile Gln Glu Thr Met Gln Ala Thr Ile His Val Pro Ala Gln
    290                 295                 300 cac gag gac ggc ccc gag gac gac cct cag ctg gtc ggc atc acc gcc      960
His Glu Asp Gly Pro Glu Asp Asp Pro Gln Leu Val Gly Ile Thr Ala
305                 310                 315                 320 cgg aac atc ccc aga ggc ccc cag ctg gcc gcc cag aac ctg ggc atc     1008
Arg Asn Ile Pro Arg Gly Pro Gln Leu Ala Ala Gln Asn Leu Gly Ile
                325                 330                 335 agc ctg gcc aac ctg ctg ctg tcc aag ggc gcc aag aac atc ctg gac     1056
Ser Leu Ala Asn Leu Leu Leu Ser Lys Gly Ala Lys Asn Ile Leu Asp
            340                 345                 350 gtg gcc cgg cag ctg aac gac gcc cac tgatga                          1089
Val Ala Arg Gln Leu Asn Asp Ala His
        355                 360

<210> SEQ ID NO 2
<211> LENGTH: 361
<212> TYPE: PRT
<213> ORGANISM: Artificial Sequence
<220> FEATURE:
<223> OTHER INFORMATION: [CDS]:1..1083 from SEQ ID NO 1

<400> SEQUENCE: 2

Met Ser Gly Asn Gly Asn Ala Ala Ala Thr Ala Glu Glu Asn Ser Pro
1               5                   10                  15

Lys Met Arg Val Ile Arg Val Gly Thr Arg Lys Ser Gln Leu Ala Arg
            20                  25                  30
```

```
Ile Gln Thr Asp Ser Val Val Ala Thr Leu Lys Ala Ser Tyr Pro Gly
             35                  40                  45

Leu Gln Phe Glu Ile Ile Ala Met Ser Thr Thr Gly Asp Lys Ile Leu
 50                  55                  60

Asp Thr Ala Leu Ser Lys Ile Gly Glu Lys Ser Leu Phe Thr Lys Glu
 65                  70                  75                  80

Leu Glu His Ala Leu Glu Lys Asn Glu Val Asp Leu Val His Ser
                 85                  90                  95

Leu Lys Asp Leu Pro Thr Val Leu Pro Pro Gly Phe Thr Ile Gly Ala
                100                 105                 110

Ile Cys Lys Arg Glu Asn Pro His Asp Ala Val Val Phe His Pro Lys
            115                 120                 125

Phe Val Gly Lys Thr Leu Glu Thr Leu Pro Glu Lys Ser Val Val Gly
        130                 135                 140

Thr Ser Ser Leu Arg Arg Ala Ala Gln Leu Gln Arg Lys Phe Pro His
145                 150                 155                 160

Leu Glu Phe Arg Ser Ile Arg Gly Asn Leu Asn Thr Arg Leu Arg Lys
                165                 170                 175

Leu Asp Glu Gln Gln Glu Phe Ser Ala Ile Leu Ala Thr Ala Gly
                180                 185                 190

Leu Gln Arg Met Gly Trp His Asn Arg Val Gly Gln Ile Leu His Pro
            195                 200                 205

Glu Glu Cys Met Tyr Ala Val Gly Gln Gly Ala Leu Gly Val Glu Val
        210                 215                 220

Arg Ala Lys Asp Gln Asp Ile Leu Asp Leu Val Gly Val Leu His Asp
225                 230                 235                 240

Pro Glu Thr Leu Leu Arg Cys Ile Ala Glu Arg Ala Phe Leu Arg His
                245                 250                 255

Leu Glu Gly Gly Cys Ser Val Pro Val Ala Val His Thr Ala Met Lys
                260                 265                 270

Asp Gly Gln Leu Tyr Leu Thr Gly Gly Val Trp Ser Leu Asp Gly Ser
            275                 280                 285

Asp Ser Ile Gln Glu Thr Met Gln Ala Thr Ile His Val Pro Ala Gln
290                 295                 300

His Glu Asp Gly Pro Glu Asp Pro Gln Leu Val Gly Ile Thr Ala
305                 310                 315                 320

Arg Asn Ile Pro Arg Gly Pro Gln Leu Ala Ala Gln Asn Leu Gly Ile
                325                 330                 335

Ser Leu Ala Asn Leu Leu Leu Ser Lys Gly Ala Lys Asn Ile Leu Asp
            340                 345                 350

Val Ala Arg Gln Leu Asn Asp Ala His
            355                 360

<210> SEQ ID NO 3
<211> LENGTH: 1038
<212> TYPE: DNA
<213> ORGANISM: Artificial Sequence
<220> FEATURE:
<223> OTHER INFORMATION: Optimized codon sequence coding for human
      erytroid PBGD
<220> FEATURE:
<221> NAME/KEY: CDS
<222> LOCATION: 1..1032
<223> OTHER INFORMATION: /codon_start="1"
      /transl_table=1

<400> SEQUENCE: 3
```

```
atg cgg gtg atc aga gtg ggc acc cgg aag agc cag ctg gcc cgg atc      48
Met Arg Val Ile Arg Val Gly Thr Arg Lys Ser Gln Leu Ala Arg Ile
1               5                   10                  15 cag acc gac agc gtg gtg gcc acc ctg aag gcc tcc tac ccc ggc ctg      96
Gln Thr Asp Ser Val Val Ala Thr Leu Lys Ala Ser Tyr Pro Gly Leu
                20                  25                  30 cag ttc gag atc att gcc atg agc acc acc ggc gac aag atc ctg gac     144
Gln Phe Glu Ile Ile Ala Met Ser Thr Thr Gly Asp Lys Ile Leu Asp
            35                  40                  45 acc gcc ctg agc aag atc ggc gag aag agc ctg ttc aca aaa gag ctg     192
Thr Ala Leu Ser Lys Ile Gly Glu Lys Ser Leu Phe Thr Lys Glu Leu
        50                  55                  60 gaa cac gcc ctg gaa aag aac gag gtg gac ctg gtg gtg cac agc ctg     240
Glu His Ala Leu Glu Lys Asn Glu Val Asp Leu Val Val His Ser Leu
65                  70                  75                  80 aag gac ctg ccc acc gtg ctg ccc cct ggc ttc acc atc ggc gcc atc     288
Lys Asp Leu Pro Thr Val Leu Pro Pro Gly Phe Thr Ile Gly Ala Ile
                85                  90                  95 tgc aag aga gag aac ccc cac gac gcc gtg gtg ttc cac cct aag ttc     336
Cys Lys Arg Glu Asn Pro His Asp Ala Val Val Phe His Pro Lys Phe
            100                 105                 110 gtg ggc aag aca ctg gaa acc ctg ccc gag aag tcc gtg gtg ggc acc     384
Val Gly Lys Thr Leu Glu Thr Leu Pro Glu Lys Ser Val Val Gly Thr
        115                 120                 125 agc agc ctg cgg aga gcc gcc cag ctg cag cgg aag ttc ccc cac ctg     432
Ser Ser Leu Arg Arg Ala Ala Gln Leu Gln Arg Lys Phe Pro His Leu
130                 135                 140 gaa ttt cgg agc atc cgg ggc aac ctg aac acc cgg ctg cgg aag ctg     480
Glu Phe Arg Ser Ile Arg Gly Asn Leu Asn Thr Arg Leu Arg Lys Leu
145                 150                 155                 160 gac gag cag cag gaa ttt tcc gct atc atc ctg gcc aca gcc gga ctg     528
Asp Glu Gln Gln Glu Phe Ser Ala Ile Ile Leu Ala Thr Ala Gly Leu
                165                 170                 175 cag cgg atg ggc tgg cac aac aga gtg ggc cag atc ctg cac ccc gag     576
Gln Arg Met Gly Trp His Asn Arg Val Gly Gln Ile Leu His Pro Glu
            180                 185                 190 gaa tgc atg tac gcc gtg ggc cag gga gcc ctg ggc gtg gaa gtg cgg     624
Glu Cys Met Tyr Ala Val Gly Gln Gly Ala Leu Gly Val Glu Val Arg
        195                 200                 205 gcc aag gac cag gac atc ctg gat ctg gtg ggc gtg ctg cat gac ccc     672
Ala Lys Asp Gln Asp Ile Leu Asp Leu Val Gly Val Leu His Asp Pro
210                 215                 220 gag aca ctg ctg cgg tgt atc gcc gag cgg gcc ttc ctg cgg cac ctg     720
Glu Thr Leu Leu Arg Cys Ile Ala Glu Arg Ala Phe Leu Arg His Leu
225                 230                 235                 240 gaa ggc ggc tgc agc gtg ccc gtg gcc gtg cac acc gcc atg aag gac     768
Glu Gly Gly Cys Ser Val Pro Val Ala Val His Thr Ala Met Lys Asp
                245                 250                 255 gga cag ctg tac ctg aca ggc ggc gtg tgg agc ctg gac ggc agc gac     816
Gly Gln Leu Tyr Leu Thr Gly Gly Val Trp Ser Leu Asp Gly Ser Asp
            260                 265                 270 agc atc cag gag acc atg cag gcc acc atc cac gtg ccc gcc cag cac     864
Ser Ile Gln Glu Thr Met Gln Ala Thr Ile His Val Pro Ala Gln His
        275                 280                 285 gag gac ggc ccc gag gac gac cct cag ctg gtc ggc atc acc gcc cgg     912
Glu Asp Gly Pro Glu Asp Asp Pro Gln Leu Val Gly Ile Thr Ala Arg
290                 295                 300 aac atc ccc aga ggc ccc cag ctg gcc gcc cag aac ctg ggc atc agc     960
Asn Ile Pro Arg Gly Pro Gln Leu Ala Ala Gln Asn Leu Gly Ile Ser
305                 310                 315                 320
```

-continued

```
ctg gcc aac ctg ctg ctg tcc aag ggc gcc aag aac atc ctg gac gtg      1008
Leu Ala Asn Leu Leu Leu Ser Lys Gly Ala Lys Asn Ile Leu Asp Val
                325                 330                 335 gcc cgg cag ctg aac gac gcc cac tgatga                                1038
Ala Arg Gln Leu Asn Asp Ala His
            340
```

<210> SEQ ID NO 4
<211> LENGTH: 344
<212> TYPE: PRT
<213> ORGANISM: Artificial Sequence
<220> FEATURE:
<223> OTHER INFORMATION: [CDS]:1..1032 from SEQ ID NO 3

<400> SEQUENCE: 4

Met Arg Val Ile Arg Val Gly Thr Arg Lys Ser Gln Leu Ala Arg Ile
1               5                   10                  15

Gln Thr Asp Ser Val Val Ala Thr Leu Lys Ala Ser Tyr Pro Gly Leu
                20                  25                  30

Gln Phe Glu Ile Ile Ala Met Ser Thr Thr Gly Asp Lys Ile Leu Asp
            35                  40                  45

Thr Ala Leu Ser Lys Ile Gly Glu Lys Ser Leu Phe Thr Lys Glu Leu
    50                  55                  60

Glu His Ala Leu Glu Lys Asn Glu Val Asp Leu Val Val His Ser Leu
65                  70                  75                  80

Lys Asp Leu Pro Thr Val Leu Pro Pro Gly Phe Thr Ile Gly Ala Ile
                85                  90                  95

Cys Lys Arg Glu Asn Pro His Asp Ala Val Val Phe His Pro Lys Phe
            100                 105                 110

Val Gly Lys Thr Leu Glu Thr Leu Pro Glu Lys Ser Val Val Gly Thr
    115                 120                 125

Ser Ser Leu Arg Arg Ala Ala Gln Leu Gln Arg Lys Phe Pro His Leu
130                 135                 140

Glu Phe Arg Ser Ile Arg Gly Asn Leu Asn Thr Arg Leu Arg Lys Leu
145                 150                 155                 160

Asp Glu Gln Gln Glu Phe Ser Ala Ile Ile Leu Ala Thr Ala Gly Leu
                165                 170                 175

Gln Arg Met Gly Trp His Asn Arg Val Gly Gln Ile Leu His Pro Glu
            180                 185                 190

Glu Cys Met Tyr Ala Val Gly Gln Gly Ala Leu Gly Val Glu Val Arg
    195                 200                 205

Ala Lys Asp Gln Asp Ile Leu Asp Leu Val Gly Val Leu His Asp Pro
210                 215                 220

Glu Thr Leu Leu Arg Cys Ile Ala Glu Arg Ala Phe Leu Arg His Leu
225                 230                 235                 240

Glu Gly Gly Cys Ser Val Pro Val Ala Val His Thr Ala Met Lys Asp
                245                 250                 255

Gly Gln Leu Tyr Leu Thr Gly Gly Val Trp Ser Leu Asp Gly Ser Asp
            260                 265                 270

Ser Ile Gln Glu Thr Met Gln Ala Thr Ile His Val Pro Ala Gln His
    275                 280                 285

Glu Asp Gly Pro Glu Asp Asp Pro Gln Leu Val Gly Ile Thr Ala Arg
290                 295                 300

Asn Ile Pro Arg Gly Pro Gln Leu Ala Ala Gln Asn Leu Gly Ile Ser
305                 310                 315                 320

```
Leu Ala Asn Leu Leu Leu Ser Lys Gly Ala Lys Asn Ile Leu Asp Val
            325                 330                 335

Ala Arg Gln Leu Asn Asp Ala His
            340
```

<210> SEQ ID NO 5
<211> LENGTH: 1089
<212> TYPE: DNA
<213> ORGANISM: Artificial Sequence
<220> FEATURE:
<223> OTHER INFORMATION: codon optimized sequence encoding hkPBGD[N340S, I291M]
<220> FEATURE:
<221> NAME/KEY: CDS
<222> LOCATION: 1..1083
<223> OTHER INFORMATION: /codon_start="1"
      /transl_table=1

<400> SEQUENCE: 5

```
atg agc ggc aac ggc aac gcc gca gcc acc gcc gag gaa aac agc ccc        48
Met Ser Gly Asn Gly Asn Ala Ala Ala Thr Ala Glu Glu Asn Ser Pro
1               5                   10                  15 aag atg cgg gtg atc aga gtg ggc acc cgg aag agc cag ctg gcc cgg        96
Lys Met Arg Val Ile Arg Val Gly Thr Arg Lys Ser Gln Leu Ala Arg
            20                  25                  30 atc cag acc gac agc gtg gtg gcc acc ctg aag gcc tcc tac ccc ggc       144
Ile Gln Thr Asp Ser Val Val Ala Thr Leu Lys Ala Ser Tyr Pro Gly
        35                  40                  45 ctg cag ttc gag atc att gcc atg agc acc acc ggc gac aag atc ctg       192
Leu Gln Phe Glu Ile Ile Ala Met Ser Thr Thr Gly Asp Lys Ile Leu
    50                  55                  60 gac acc gcc ctg agc aag atc ggc gag aag agc ctg ttc aca aaa gag       240
Asp Thr Ala Leu Ser Lys Ile Gly Glu Lys Ser Leu Phe Thr Lys Glu
65                  70                  75                  80 ctg gaa cac gcc ctg gaa aag aac gag gtg gac ctg gtg gtg cac agc       288
Leu Glu His Ala Leu Glu Lys Asn Glu Val Asp Leu Val Val His Ser
                85                  90                  95 ctg aag gac ctg ccc acc gtg ctg ccc cct ggc ttc acc atc ggc gcc       336
Leu Lys Asp Leu Pro Thr Val Leu Pro Pro Gly Phe Thr Ile Gly Ala
            100                 105                 110 atc tgc aag aga gag aac ccc cac gac gcc gtg gtg ttc cac cct aag       384
Ile Cys Lys Arg Glu Asn Pro His Asp Ala Val Val Phe His Pro Lys
        115                 120                 125 ttc gtg ggc aag aca ctg gaa acc ctg ccc gag aag tcc gtg gtg ggc       432
Phe Val Gly Lys Thr Leu Glu Thr Leu Pro Glu Lys Ser Val Val Gly
    130                 135                 140 acc agc agc ctg cgg aga gcc gcc cag ctg cag cgg aag ttc ccc cac       480
Thr Ser Ser Leu Arg Arg Ala Ala Gln Leu Gln Arg Lys Phe Pro His
145                 150                 155                 160 ctg gaa ttt cgg agc atc cgg ggc aac ctg aac acc cgg ctg cgg aag       528
Leu Glu Phe Arg Ser Ile Arg Gly Asn Leu Asn Thr Arg Leu Arg Lys
                165                 170                 175 ctg gac gag cag cag gaa ttt tcc gct atc atc ctg gcc aca gcc gga       576
Leu Asp Glu Gln Gln Glu Phe Ser Ala Ile Ile Leu Ala Thr Ala Gly
            180                 185                 190 ctg cag cgg atg ggc tgg cac aac aga gtg ggc cag atc ctg cac ccc       624
Leu Gln Arg Met Gly Trp His Asn Arg Val Gly Gln Ile Leu His Pro
        195                 200                 205 gag gaa tgc atg tac gcc gtg ggc cag gga gcc ctg ggc gtg gaa gtg       672
Glu Glu Cys Met Tyr Ala Val Gly Gln Gly Ala Leu Gly Val Glu Val
    210                 215                 220 cgg gcc aag gac cag gac atc ctg gat ctg gtg ggc gtg ctg cat gac       720
Arg Ala Lys Asp Gln Asp Ile Leu Asp Leu Val Gly Val Leu His Asp
```

```
Arg Ala Lys Asp Gln Asp Ile Leu Asp Leu Val Gly Val Leu His Asp
225                 230                 235                 240 ccc gag aca ctg ctg cgg tgt atc gcc gag cgg gcc ttc ctg cgg cac      768
Pro Glu Thr Leu Leu Arg Cys Ile Ala Glu Arg Ala Phe Leu Arg His
                    245                 250                 255 ctg gaa ggc ggc tgc agc gtg ccc gtg gcc gtg cac acc gcc atg aag      816
Leu Glu Gly Gly Cys Ser Val Pro Val Ala Val His Thr Ala Met Lys
                260                 265                 270 gac gga cag ctg tac ctg aca ggc ggc gtg tgg agc ctg gac ggc agc      864
Asp Gly Gln Leu Tyr Leu Thr Gly Gly Val Trp Ser Leu Asp Gly Ser
            275                 280                 285 gac agc atg cag gag acc atg cag gcc acc atc cac gtg ccc gcc cag      912
Asp Ser Met Gln Glu Thr Met Gln Ala Thr Ile His Val Pro Ala Gln
        290                 295                 300 cac gag gac ggc ccc gag gac gac cct cag ctg gtc ggc atc acc gcc      960
His Glu Asp Gly Pro Glu Asp Asp Pro Gln Leu Val Gly Ile Thr Ala
305                 310                 315                 320 cgg aac atc ccc aga ggc ccc cag ctg gcc gcc cag aac ctg ggc atc     1008
Arg Asn Ile Pro Arg Gly Pro Gln Leu Ala Ala Gln Asn Leu Gly Ile
                    325                 330                 335 agc ctg gcc agc ctg ctg ctg tcc aag ggc gcc aag aac atc ctg gac     1056
Ser Leu Ala Ser Leu Leu Leu Ser Lys Gly Ala Lys Asn Ile Leu Asp
                340                 345                 350 gtg gcc cgg cag ctg aac gac gcc cac tgatga                         1089
Val Ala Arg Gln Leu Asn Asp Ala His
            355                 360

<210> SEQ ID NO 6
<211> LENGTH: 361
<212> TYPE: PRT
<213> ORGANISM: Artificial Sequence
<220> FEATURE:
<223> OTHER INFORMATION: [CDS]:1..1083 from SEQ ID NO 5

<400> SEQUENCE: 6

Met Ser Gly Asn Gly Asn Ala Ala Ala Thr Ala Glu Glu Asn Ser Pro
1               5                   10                  15

Lys Met Arg Val Ile Arg Val Gly Thr Arg Lys Ser Gln Leu Ala Arg
                20                  25                  30

Ile Gln Thr Asp Ser Val Val Ala Thr Leu Lys Ala Ser Tyr Pro Gly
            35                  40                  45

Leu Gln Phe Glu Ile Ile Ala Met Ser Thr Thr Gly Asp Lys Ile Leu
        50                  55                  60

Asp Thr Ala Leu Ser Lys Ile Gly Glu Lys Ser Leu Phe Thr Lys Glu
65                  70                  75                  80

Leu Glu His Ala Leu Glu Lys Asn Glu Val Asp Leu Val Val His Ser
                85                  90                  95

Leu Lys Asp Leu Pro Thr Val Leu Pro Pro Gly Phe Thr Ile Gly Ala
            100                 105                 110

Ile Cys Lys Arg Glu Asn Pro His Asp Ala Val Val Phe His Pro Lys
        115                 120                 125

Phe Val Gly Lys Thr Leu Glu Thr Leu Pro Glu Lys Ser Val Val Gly
    130                 135                 140

Thr Ser Ser Leu Arg Arg Ala Ala Gln Leu Gln Arg Lys Phe Pro His
145                 150                 155                 160

Leu Glu Phe Arg Ser Ile Arg Gly Asn Leu Asn Thr Arg Leu Arg Lys
                165                 170                 175

Leu Asp Glu Gln Gln Glu Phe Ser Ala Ile Ile Leu Ala Thr Ala Gly
```

-continued

```
            180                 185                 190
Leu Gln Arg Met Gly Trp His Asn Arg Val Gly Gln Ile Leu His Pro
        195                 200                 205
Glu Glu Cys Met Tyr Ala Val Gly Gln Gly Ala Leu Gly Val Glu Val
        210                 215                 220
Arg Ala Lys Asp Gln Asp Ile Leu Asp Leu Val Gly Val Leu His Asp
225                 230                 235                 240
Pro Glu Thr Leu Leu Arg Cys Ile Ala Glu Arg Ala Phe Leu Arg His
                245                 250                 255
Leu Glu Gly Gly Cys Ser Val Pro Val Ala Val His Thr Ala Met Lys
            260                 265                 270
Asp Gly Gln Leu Tyr Leu Thr Gly Gly Val Trp Ser Leu Asp Gly Ser
        275                 280                 285
Asp Ser Met Gln Glu Thr Met Gln Ala Thr Ile His Val Pro Ala Gln
        290                 295                 300
His Glu Asp Gly Pro Glu Asp Pro Gln Leu Val Gly Ile Thr Ala
305                 310                 315                 320
Arg Asn Ile Pro Arg Gly Pro Gln Leu Ala Ala Gln Asn Leu Gly Ile
                325                 330                 335
Ser Leu Ala Ser Leu Leu Ser Lys Gly Ala Lys Asn Ile Leu Asp
            340                 345                 350
Val Ala Arg Gln Leu Asn Asp Ala His
            355                 360

<210> SEQ ID NO 7
<211> LENGTH: 267
<212> TYPE: PRT
<213> ORGANISM: Homo sapiens
<220> FEATURE:
<223> OTHER INFORMATION: >sp 2647 OA1_HUMAN Apolipoprotein A-I
      OS=Homo sapiens GN=APOA1 PE=1 SV=1

<400> SEQUENCE: 7

Met Lys Ala Ala Val Leu Thr Leu Ala Val Leu Phe Leu Thr Gly Ser
1               5                   10                  15
Gln Ala Arg His Phe Trp Gln Gln Asp Glu Pro Pro Gln Ser Pro Trp
            20                  25                  30
Asp Arg Val Lys Asp Leu Ala Thr Val Tyr Val Asp Val Leu Lys Asp
        35                  40                  45
Ser Gly Arg Asp Tyr Val Ser Gln Phe Glu Gly Ser Ala Leu Gly Lys
    50                  55                  60
Gln Leu Asn Leu Lys Leu Leu Asp Asn Trp Asp Ser Val Thr Ser Thr
65                  70                  75                  80
Phe Ser Lys Leu Arg Glu Gln Leu Gly Pro Val Thr Gln Glu Phe Trp
                85                  90                  95
Asp Asn Leu Glu Lys Glu Thr Glu Gly Leu Arg Gln Glu Met Ser Lys
            100                 105                 110
Asp Leu Glu Glu Val Lys Ala Lys Val Gln Pro Tyr Leu Asp Asp Phe
        115                 120                 125
Gln Lys Lys Trp Gln Glu Glu Met Glu Leu Tyr Arg Gln Lys Val Glu
    130                 135                 140
Pro Leu Arg Ala Glu Leu Gln Glu Gly Ala Arg Gln Lys Leu His Glu
145                 150                 155                 160
Leu Gln Glu Lys Leu Ser Pro Leu Gly Glu Glu Met Arg Asp Arg Ala
                165                 170                 175
```

```
Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265
```

<210> SEQ ID NO 8
<211> LENGTH: 669
<212> TYPE: DNA
<213> ORGANISM: Artificial Sequence
<220> FEATURE:
<223> OTHER INFORMATION: Human AAT promoter combined with the mouse
      albumin gene enhancer (Ealb) element

<400> SEQUENCE: 8

```
ggttcctaga ttacactaca cattctgcaa gcatagcaca gagcaatgtt ctactttaat      60
tactttcatt ttcttgtatc ctcacagcct agaaaataac ctgcgttaca gcatccactc     120
agtatccctt gagcatgagg tgacactact aacatagggg acgagatggt actttgtgtc     180
tcctgctctg tcagcagggc acagtacttg ctgataccag gaatgtttg ttcttaaata      240
ccatcattcc ggacgtgttt gccttggcca gttttccatg tacatgcaga aagaagtttg     300
gactgatcaa tacagtcctc tgcctttaaa gcaataggaa aaggccaact tgtctacgtt     360
tagtatgtgg ctgtagatct gtacccgcca ccccctccac cttggacaca ggacgctgtg     420
gtttctgagc caggtacaat gactcctttc ggtaagtgca gtggaagctg tacactgccc     480
aggcaaagcg tccgggcagc gtaggcgggc gactcagatc ccagccagtg gacttagccc     540
ctgtttgctc ctccgataac tggggtgacc ttggttaata ttcaccagca gcctcccccg     600
ttgcccctct ggatccactg cttaaatacg gacgaggaca gggccctgtc tcctcagctt     660
caggcacca                                                             669
```

<210> SEQ ID NO 9
<211> LENGTH: 351
<212> TYPE: DNA
<213> ORGANISM: Artificial Sequence
<220> FEATURE:
<223> OTHER INFORMATION: Synthetic construct of two ADRES repeats in
      tandem

<400> SEQUENCE: 9

```
gcgcaaagtc aacacaagcc tctccaccgt gtgtccatgt ttatgtgtat gcgctgtgcc      60
ccgtcatgcc acctggacgc agggactcca gtgacctctc cttgcacaag cctctgctgg     120
tttgggaaag attggcatga catcagccaa gctctggcct tgccttttt ccctcgagcg      180
caaagtcaac acaagcctct ccaccgtgtg tccatgttta tgtgtatgcg ctgtgccccg     240
tcatgccacc tggacgcagg gactccagtg acctctcctt gcacaagcct ctgctggttt     300
gggaaagatt ggcatgacat cagccaagct ctggccttgc cttttttccc t              351
```

<210> SEQ ID NO 10
<211> LENGTH: 145

```
<212> TYPE: DNA
<213> ORGANISM: Adeno-associated virus - 2
<220> FEATURE:
<223> OTHER INFORMATION: ITR-5'

<400> SEQUENCE: 10
ttggccactc cctctctgcg cgctcgctcg ctcactgagg ccgggcgacc aaaggtcgcc    60
cgacgcccgg gctttgcccg ggcggcctca gtgagcgagc gagcgcgcag agagggagtg   120
gccaactcca tcactagggg ttcct                                         145

<210> SEQ ID NO 11
<211> LENGTH: 146
<212> TYPE: DNA
<213> ORGANISM: Adeno-associated virus - 2
<220> FEATURE:
<223> OTHER INFORMATION: ITR-3'

<400> SEQUENCE: 11
ttggccactc cctctctgcg cgctcgctcg ctcactgagg ccgcccgggc aaagcccggg    60
cgtcgggcga cctttggtcg cccggcctca gtgagcgagc gagcgcgcag agagggagtg   120
gccaactcca tcactagggg ttcccc                                        146

<210> SEQ ID NO 12
<211> LENGTH: 1815
<212> TYPE: DNA
<213> ORGANISM: Artificial Sequence
<220> FEATURE:
<223> OTHER INFORMATION: Codon optimized sequence coding for fusion
      protein of human ApoA1 with hkPBGD-SM
<220> FEATURE:
<221> NAME/KEY: CDS
<222> LOCATION: 1..1815
<223> OTHER INFORMATION: /transl_table=1

<400> SEQUENCE: 12 atg gat gaa ccc ccc cag agc ccc tgg gat cga gtg aag gac ctg gcc     48
Met Asp Glu Pro Pro Gln Ser Pro Trp Asp Arg Val Lys Asp Leu Ala
1               5                   10                  15 act gtg tac gtg gat gtg ctc aaa gac agc ggc aga gac tat gtg tcc     96
Thr Val Tyr Val Asp Val Leu Lys Asp Ser Gly Arg Asp Tyr Val Ser
                20                  25                  30 cag ttt gaa ggc tcc gcc ttg gga aaa cag cta aac cta aag ctc ctt    144
Gln Phe Glu Gly Ser Ala Leu Gly Lys Gln Leu Asn Leu Lys Leu Leu
            35                  40                  45 gac aac tgg gac agc gtg acc tcc acc ttc agc aag ctg cgc gaa cag    192
Asp Asn Trp Asp Ser Val Thr Ser Thr Phe Ser Lys Leu Arg Glu Gln
        50                  55                  60 ctc ggc cct gtg acc cag gag ttc tgg gat aac ctg gaa aag gag aca    240
Leu Gly Pro Val Thr Gln Glu Phe Trp Asp Asn Leu Glu Lys Glu Thr
65                  70                  75                  80 gag ggc ctg agg cag gag atg agc aag gat ctg gag gag gtg aag gcc    288
Glu Gly Leu Arg Gln Glu Met Ser Lys Asp Leu Glu Glu Val Lys Ala
                85                  90                  95 aag gtg cag ccc tac ctg gac gac ttc cag aag aag tgg cag gag gag    336
Lys Val Gln Pro Tyr Leu Asp Asp Phe Gln Lys Lys Trp Gln Glu Glu
            100                 105                 110 atg gag ctc tac cgc cag aag gtg gag ccg ctg cgc gca gag ctc caa    384
Met Glu Leu Tyr Arg Gln Lys Val Glu Pro Leu Arg Ala Glu Leu Gln
        115                 120                 125 gag ggc gcg cgc cag aag ctg cac gag ctg caa gag aag ctg agc cca    432
Glu Gly Ala Arg Gln Lys Leu His Glu Leu Gln Glu Lys Leu Ser Pro
    130                 135                 140
```

```
ctg ggc gag gag atg cgc gac cgc gcg cgc gcc cat gtg gac gcg ctg      480
Leu Gly Glu Glu Met Arg Asp Arg Ala Arg Ala His Val Asp Ala Leu
145                 150                 155                 160 cgc acg cat ctg gcc ccc tac agc gac gag ctg cgc cag cgc ttg gcc      528
Arg Thr His Leu Ala Pro Tyr Ser Asp Glu Leu Arg Gln Arg Leu Ala
                165                 170                 175 gcg cgc ctt gag gct ctc aag gag aac ggc ggc gcc aga ctg gcc gag      576
Ala Arg Leu Glu Ala Leu Lys Glu Asn Gly Gly Ala Arg Leu Ala Glu
            180                 185                 190 tac cac gcc aag gcc acc gag cat ctg agc acg ctc agc gag aag gcc      624
Tyr His Ala Lys Ala Thr Glu His Leu Ser Thr Leu Ser Glu Lys Ala
        195                 200                 205 aag ccc gcg ctc gag gac ctc cgc caa ggc ctg ctg ccc gtg ctg gag      672
Lys Pro Ala Leu Glu Asp Leu Arg Gln Gly Leu Leu Pro Val Leu Glu
210                 215                 220 agc ttc aag gtc agc ttc ctg agc gct ctc gag gag tac act aag aag      720
Ser Phe Lys Val Ser Phe Leu Ser Ala Leu Glu Glu Tyr Thr Lys Lys
225                 230                 235                 240 ctc aac acc cag agc ggc aac ggc aac gcc gca gcc acc gcc gag gaa      768
Leu Asn Thr Gln Ser Gly Asn Gly Asn Ala Ala Ala Thr Ala Glu Glu
                245                 250                 255 aac agc ccc aag atg cgg gtg atc aga gtg ggc acc cgg aag agc cag      816
Asn Ser Pro Lys Met Arg Val Ile Arg Val Gly Thr Arg Lys Ser Gln
            260                 265                 270 ctg gcc cgg atc cag acc gac agc gtg gtg gcc acc ctg aag gcc tcc      864
Leu Ala Arg Ile Gln Thr Asp Ser Val Val Ala Thr Leu Lys Ala Ser
        275                 280                 285 tac ccc ggc ctg cag ttc gag atc att gcc atg agc acc acc ggc gac      912
Tyr Pro Gly Leu Gln Phe Glu Ile Ile Ala Met Ser Thr Thr Gly Asp
    290                 295                 300 aag atc ctg gac acc gcc ctg agc aag atc ggc gag aag agc ctg ttc      960
Lys Ile Leu Asp Thr Ala Leu Ser Lys Ile Gly Glu Lys Ser Leu Phe
305                 310                 315                 320 aca aaa gag ctg gaa cac gcc ctg gaa aag aac gag gtg gac ctg gtg     1008
Thr Lys Glu Leu Glu His Ala Leu Glu Lys Asn Glu Val Asp Leu Val
                325                 330                 335 gtg cac agc ctg aag gac ctg ccc acc gtg ctg ccc cct ggc ttc acc     1056
Val His Ser Leu Lys Asp Leu Pro Thr Val Leu Pro Pro Gly Phe Thr
            340                 345                 350 atc ggc gcc atc tgc aag aga gag aac ccc cac gac gcc gtg gtg ttc     1104
Ile Gly Ala Ile Cys Lys Arg Glu Asn Pro His Asp Ala Val Val Phe
        355                 360                 365 cac cct aag ttc gtg ggc aag aca ctg gaa acc ctg ccc gag aag tcc     1152
His Pro Lys Phe Val Gly Lys Thr Leu Glu Thr Leu Pro Glu Lys Ser
    370                 375                 380 gtg gtg ggc acc agc agc ctg cgg aga gcc gcc cag ctg cag cgg aag     1200
Val Val Gly Thr Ser Ser Leu Arg Arg Ala Ala Gln Leu Gln Arg Lys
385                 390                 395                 400 ttc ccc cac ctg gaa ttt cgg agc atc cgg ggc aac ctg aac acc cgg     1248
Phe Pro His Leu Glu Phe Arg Ser Ile Arg Gly Asn Leu Asn Thr Arg
                405                 410                 415 ctg cgg aag ctg gac gag cag cag gaa ttt tcc gct atc atc ctg gcc     1296
Leu Arg Lys Leu Asp Glu Gln Gln Glu Phe Ser Ala Ile Ile Leu Ala
            420                 425                 430 aca gcc gga ctg cag cgg atg ggc tgg cac aac aga gtg ggc cag atc     1344
Thr Ala Gly Leu Gln Arg Met Gly Trp His Asn Arg Val Gly Gln Ile
        435                 440                 445 ctg cac ccc gag gaa tgc atg tac gcc gtg ggc cag gga gcc ctg ggc     1392
Leu His Pro Glu Glu Cys Met Tyr Ala Val Gly Gln Gly Ala Leu Gly
```

```
                    450                 455                 460
gtg gaa gtg cgg gcc aag gac cag gac atc ctg gat ctg gtg ggc gtg     1440
Val Glu Val Arg Ala Lys Asp Gln Asp Ile Leu Asp Leu Val Gly Val
465                 470                 475                 480 ctg cat gac ccc gag aca ctg ctg cgg tgt atc gcc gag cgg gcc ttc     1488
Leu His Asp Pro Glu Thr Leu Leu Arg Cys Ile Ala Glu Arg Ala Phe
                485                 490                 495 ctg cgg cac ctg gaa ggc ggc tgc agc gtg ccc gtg gcc gtg cac acc     1536
Leu Arg His Leu Glu Gly Gly Cys Ser Val Pro Val Ala Val His Thr
            500                 505                 510 gcc atg aag gac gga cag ctg tac ctg aca ggc ggc gtg tgg agc ctg     1584
Ala Met Lys Asp Gly Gln Leu Tyr Leu Thr Gly Gly Val Trp Ser Leu
        515                 520                 525 gac ggc agc gac agc atg cag gag acc atg cag gcc acc atc cac gtg     1632
Asp Gly Ser Asp Ser Met Gln Glu Thr Met Gln Ala Thr Ile His Val
    530                 535                 540 ccc gcc cag cac gag gac ggc ccc gag gac gac cct cag ctg gtc ggc     1680
Pro Ala Gln His Glu Asp Gly Pro Glu Asp Asp Pro Gln Leu Val Gly
545                 550                 555                 560 atc acc gcc cgg aac atc ccc aga ggc ccc cag ctg gcc gcc cag aac     1728
Ile Thr Ala Arg Asn Ile Pro Arg Gly Pro Gln Leu Ala Ala Gln Asn
                565                 570                 575 ctg ggc atc agc ctg gcc agc ctg ctg ctg tcc aag ggc gcc aag aac     1776
Leu Gly Ile Ser Leu Ala Ser Leu Leu Leu Ser Lys Gly Ala Lys Asn
            580                 585                 590 atc ctg gac gtg gcc cgg cag ctg aac gac gcc cac tga                 1815
Ile Leu Asp Val Ala Arg Gln Leu Asn Asp Ala His
        595                 600

<210> SEQ ID NO 13
<211> LENGTH: 604
<212> TYPE: PRT
<213> ORGANISM: Artificial Sequence
<220> FEATURE:
<223> OTHER INFORMATION: [CDS]:1..1815 from SEQ ID NO 12

<400> SEQUENCE: 13

Met Asp Glu Pro Pro Gln Ser Pro Trp Asp Arg Val Lys Asp Leu Ala
1               5                   10                  15

Thr Val Tyr Val Asp Val Leu Lys Asp Ser Gly Arg Asp Tyr Val Ser
            20                  25                  30

Gln Phe Glu Gly Ser Ala Leu Gly Lys Gln Leu Asn Leu Lys Leu Leu
        35                  40                  45

Asp Asn Trp Asp Ser Val Thr Ser Thr Phe Ser Lys Leu Arg Glu Gln
    50                  55                  60

Leu Gly Pro Val Thr Gln Glu Phe Trp Asp Asn Leu Glu Lys Glu Thr
65                  70                  75                  80

Glu Gly Leu Arg Gln Glu Met Ser Lys Asp Leu Glu Glu Val Lys Ala
                85                  90                  95

Lys Val Gln Pro Tyr Leu Asp Asp Phe Gln Lys Lys Trp Gln Glu Glu
            100                 105                 110

Met Glu Leu Tyr Arg Gln Lys Val Glu Pro Leu Arg Ala Glu Leu Gln
        115                 120                 125

Glu Gly Ala Arg Gln Lys Leu His Glu Leu Gln Glu Lys Leu Ser Pro
    130                 135                 140

Leu Gly Glu Glu Met Arg Asp Arg Ala Arg Ala His Val Asp Ala Leu
145                 150                 155                 160

Arg Thr His Leu Ala Pro Tyr Ser Asp Glu Leu Arg Gln Arg Leu Ala
```

-continued

```
                165                 170                 175
Ala Arg Leu Glu Ala Leu Lys Glu Asn Gly Gly Ala Arg Leu Ala Glu
                    180                 185                 190

Tyr His Ala Lys Ala Thr Glu His Leu Ser Thr Leu Ser Glu Lys Ala
                    195                 200                 205

Lys Pro Ala Leu Glu Asp Leu Arg Gln Gly Leu Leu Pro Val Leu Glu
                    210                 215                 220

Ser Phe Lys Val Ser Phe Leu Ser Ala Leu Glu Glu Tyr Thr Lys Lys
225                 230                 235                 240

Leu Asn Thr Gln Ser Gly Asn Gly Asn Ala Ala Thr Ala Glu Glu
                    245                 250                 255

Asn Ser Pro Lys Met Arg Val Ile Arg Val Gly Thr Arg Lys Ser Gln
                    260                 265                 270

Leu Ala Arg Ile Gln Thr Asp Ser Val Val Ala Thr Leu Lys Ala Ser
                    275                 280                 285

Tyr Pro Gly Leu Gln Phe Glu Ile Ile Ala Met Ser Thr Thr Gly Asp
                    290                 295                 300

Lys Ile Leu Asp Thr Ala Leu Ser Lys Ile Gly Glu Lys Ser Leu Phe
305                 310                 315                 320

Thr Lys Glu Leu Glu His Ala Leu Glu Lys Asn Glu Val Asp Leu Val
                    325                 330                 335

Val His Ser Leu Lys Asp Leu Pro Thr Val Leu Pro Pro Gly Phe Thr
                    340                 345                 350

Ile Gly Ala Ile Cys Lys Arg Glu Asn Pro His Asp Ala Val Val Phe
                    355                 360                 365

His Pro Lys Phe Val Gly Lys Thr Leu Glu Thr Leu Pro Glu Lys Ser
                    370                 375                 380

Val Val Gly Thr Ser Ser Leu Arg Arg Ala Ala Gln Leu Gln Arg Lys
385                 390                 395                 400

Phe Pro His Leu Glu Phe Arg Ser Ile Arg Gly Asn Leu Asn Thr Arg
                    405                 410                 415

Leu Arg Lys Leu Asp Glu Gln Gln Glu Phe Ser Ala Ile Ile Leu Ala
                    420                 425                 430

Thr Ala Gly Leu Gln Arg Met Gly Trp His Asn Arg Val Gly Gln Ile
                    435                 440                 445

Leu His Pro Glu Glu Cys Met Tyr Ala Val Gly Gln Gly Ala Leu Gly
                    450                 455                 460

Val Glu Val Arg Ala Lys Asp Gln Asp Ile Leu Asp Leu Val Gly Val
465                 470                 475                 480

Leu His Asp Pro Glu Thr Leu Leu Arg Cys Ile Ala Glu Arg Ala Phe
                    485                 490                 495

Leu Arg His Leu Glu Gly Gly Cys Ser Val Pro Val Ala Val His Thr
                    500                 505                 510

Ala Met Lys Asp Gly Gln Leu Tyr Leu Thr Gly Gly Val Trp Ser Leu
                    515                 520                 525

Asp Gly Ser Asp Ser Met Gln Glu Thr Met Gln Ala Thr Ile His Val
                    530                 535                 540

Pro Ala Gln His Glu Asp Gly Pro Glu Asp Pro Gln Leu Val Gly
545                 550                 555                 560

Ile Thr Ala Arg Asn Ile Pro Arg Gly Pro Gln Leu Ala Ala Gln Asn
                    565                 570                 575

Leu Gly Ile Ser Leu Ala Ser Leu Leu Leu Ser Lys Gly Ala Lys Asn
                    580                 585                 590
```

Ile Leu Asp Val Ala Arg Gln Leu Asn Asp Ala His
        595                 600

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
gcctgcagtt cgagatcatt                                         20

<210> SEQ ID NO 15
<211> LENGTH: 16
<212> TYPE: DNA
<213> ORGANISM: Artificial Sequence
<220> FEATURE:
<223> OTHER INFORMATION: Primer

<400> SEQUENCE: 15
aggtccttca ggctgt                                             16

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
ccaaggtcat ccatgacaac                                         20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
tgtcatacca ggaaatgagc                                         20

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
gctagccttt gaatgtaacc a                                       21

<210> SEQ ID NO 19
<211> LENGTH: 25
<212> TYPE: DNA
<213> ORGANISM: Artificial Sequence
<220> FEATURE:
<223> OTHER INFORMATION: Primer

<400> SEQUENCE: 19
ccttcagaac tggtttatta gtagg                                   25

US 11,390,854 B2

HUMAN PORPHOBILINOGEN DEAMINASE DERIVED PROTEINS AND POLYNUCLEOTIDES AND USES THEREOF

RELATED APPLICATIONS

This application is a U.S. National Phase application, filed under 35 U.S.C. § 371, of International Application No. PCT/EP2017/061944, filed on May 18, 2017, which claims priority to, and the benefit of, European Patent Application No. 17382257.8, filed on May 9, 2017, the contents of each of which are incorporated by reference in their entireties.

This application claims priority to, and the benefit of, European Patent Application No. 17382257.8, filed on May 9, 2017, the contents of which are incorporated by reference in the entirety.

INCORPORATION BY REFERENCE OF SEQUENCE LISTING

The contents of the text file named "MRNA-037NO1US SeqList.txt", which was created on Nov. 4, 2019 and is 43 KB in size, are hereby incorporated by reference in their entirety.

BACKGROUND

Acute intermittent porphyria (AIP, MIM 176000) is an autosomal dominant metabolic disease characterized by a deficiency of hydroxymethylbilane synthase (HMBS), also named as porphobilinogen deaminase (PBGD). PBGD is the third enzyme of heme synthesis pathway (EC 4.3.1.8; UniProt Accession #P08397) that catalyzes the loss of ammonia from the porphobilinogen monomer (deamination) and its subsequent polymerization to a linear tetrapyrrole, which is released as hydroxymethylbilane.

A genetic defect at the PBGD locus generates a significant reduction in its activity, which in conjunction with impaired heme-mediated activation of hepatic ALAS1 (EC 2.3.1.37) leads to a marked overproduction and accumulation of δ-aminolevulinic acid, also named 5-aminolevulinic acid (ALA), and porphobilinogen (PBG) that are the porphyrin substrates between both enzymes. AIP is characterized by acute, potentially life-threatening neurological attacks that are precipitated by various drugs, reproductive hormones, and other factors. During acute attacks, the porphyrin precursors ALA and PBG accumulate in liver and serum and are excreted at high concentrations in the urine.

Current treatment is based on glucose loading and parenteral heme replenishment, which reduce the accumulation of ALA and PBG. However, recurrent hyper-activation of the hepatic heme synthesis pathway affects about 5% of patients and can be associated with neurological and metabolic manifestations and long-term complications including chronic kidney disease and increased risk of hepatocellular carcinoma. Prophylactic heme infusion is an effective strategy in some of these patients, but it induces tolerance and its frequent application may be associated with thromboembolic disease and hepatic siderosis. Chronic activation of hepatic heme synthesis is a life-threatening condition that can be cured only by allogeneic liver transplantation. However, liver transplantation has limited availability of compatible donors, and a significant morbidity and mortality.

Therefore, improved therapies remain an important need in the treatment of AIP. The present disclosure addresses this need.

SUMMARY

The present disclosure provides a polypeptide comprising a) a human non-erythropoietic housekeeping porphobilinogen deaminase (PBGD) comprising at least one amino acid mutation with respect to SEQ ID NO:2 selected from the group consisting of mutations N340S, I291M, H199Q, H120Y, and S344N; or b) a human erythropoietic PBGD comprising at least one amino acid mutation with respect to SEQ ID NO:4 selected from the group consisting of mutations N323S, I274M, H182Q, H103Y, and S327N. The polypeptides can comprise at least two, at least three, at least four or at least five amino acid mutations. The polypeptides can have enhanced or increased deaminase activity when compared to the amino acid sequence of SEQ ID NO:2 or SEQ ID NO:4. In one aspect, the modified human non-erythropoietic housekeeping PBGD comprises hkPBGD$_{[N340S]}$, hkPBGD$_{[I291M]}$, hkPBGD$_{[H199Q]}$, hkPBGD$_{[H120Y]}$, hkPBGD$_{[S344N]}$, hkPBGD$_{[N340S, I291M]}$, hkPBGD$_{[N340S, H199Q]}$, and hkPBGD$_{[N340S, H120Y]}$. In a particular aspect, the human non-erythropoietic housekeeping PBGD comprises amino acid mutations N340S and I291M with respect to SEQ ID NO:2 (hkPBGD$_{[N340S, I291M]}$). In a preferred aspect, the polypeptide has the amino acid sequence of SEQ ID NO:6.

The present disclosure also provides a modified human PBGD protein comprising at least one amino acid mutation with respect to human housekeeping PBGD enzyme of SEQ ID NO:2, wherein the modified PBGD protein is conjugated to at least one carrier polypeptide or a functionally equivalent variant thereof. The modified PBGD conjugated to at least one carrier polypeptide can comprise at least two, at least three, at least four or at least five amino acid mutations. The modified polypeptides can have enhanced or increased deaminase activity when compared to the amino acid sequence of SEQ ID NO:2 or when compared to an unconjugated modified human PBGD protein. In one aspect, the modified PBGD is covalently bound to the carrier polypeptide, or a functionally equivalent variant thereof, and forms a single polypeptide chain. In one aspect, the C-terminal end of the carrier polypeptide, or a functionally equivalent variant thereof, is bound to the N-terminal end of the modified PBGD or the N-terminal end of the carrier polypeptide, or a functionally equivalent variant thereof, is bound to the C-terminal end of the modified PBGD.

In one aspect the at least one carrier polypeptide, or a functionally equivalent variant thereof, is Apo A protein and the present disclosure provides a composition comprising: (i) an Apo A protein, or a functionally equivalent variant thereof, and (ii) a modified human PBGD protein of the present disclosure. In a particular aspect, the Apo A protein is human ApoA-I. In a preferred aspect, the human ApoA-I protein has the amino acid sequence of SEQ ID NO:7. In a particular aspect, the present disclosure provides modified ApoAI-PBGD$_{[N340S, I291M]}$ or modified PBGD$_{[N340S, I291M]}$-ApoAI. In a preferred aspect, the conjugate of human ApoAI-PBGD$_{[N340S, I291M]}$ has the amino acid sequence of SEQ ID NO:13.

The present disclosure also provides a polynucleotide, nucleic acid construct or vector comprising a nucleic acid sequence encoding a modified human PBGD protein of the present disclosure. In one aspect, the polynucleotide or nucleic acid construct has the nucleic acid sequence of SEQ ID NO:5. In one aspect, the polynucleotide or nucleic acid construct has the nucleic acid sequence of SEQ ID NO:12. The vector can further comprise additional elements or features to permit the modified human PBGD protein encoded by the nucleic acid sequence to be expressed in a tissue or cell of interest. The present disclosure also provides a host cell comprising a modified human PBGD protein of the present disclosure or a polynucleotide encoding a modified human PBGD protein of the present disclosure. The present disclosure also provides a pharmaceutical or veterinary composition comprising a modified human PBGD protein of the present disclosure or a polynucleotide encoding a modified human PBGD protein of the present disclosure.

The present disclosure also provides methods of treating, or ameliorating at least one symptom of, a condition associated with, or caused by, a deficiency in porphobilinogen deaminase in a subject in need thereof comprising administering to said subject a therapeutically effective amount of a modified human PBGD protein, a polynucleotide encoding a modified human PBGD protein, a vector comprising a polynucleotide encoding a modified human PBGD protein, a host cell comprising a modified human PBGD protein, comprising a polynucleotide encoding a modified human PBGD protein, or comprising a vector comprising a polynucleotide encoding a modified human PBGD protein, or a pharmaceutical or veterinary composition comprising a modified human PBGD protein, comprising a polynucleotide encoding a modified human PBGD protein, comprising a vector comprising a polynucleotide encoding a modified human PBGD protein or comprising a host cell as described in the instant disclosure. In one aspect, the deficiency in porphobilinogen deaminase is acute porphyria. In a particular aspect, the deficiency in porphobilinogen deaminase is acute intermittent porphyria.

The present disclosure also provides methods for increasing porphobilinogen deaminase activity in a subject in need thereof comprising administering to said subject a therapeutically effective amount of a modified human PBGD protein, a polynucleotide encoding a modified human PBGD protein, a vector comprising a polynucleotide encoding a modified human PBGD protein, a host cell comprising a modified human PBGD protein, comprising a polynucleotide encoding a modified human PBGD protein, or comprising a vector comprising a polynucleotide encoding a modified human PBGD protein, or a pharmaceutical or veterinary composition comprising a modified human PBGD protein, comprising a polynucleotide encoding a modified human PBGD protein, comprising a vector comprising a polynucleotide encoding a modified human PBGD protein or comprising a host cell as described in the instant disclosure.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents, and other references mentioned herein are incorporated by reference in their entireties for all purposes. The references cited herein are not admitted to be prior art to the claimed disclosure. In the case of conflict, the present specification, including definitions, will control. In addition, the materials, methods, and examples are illustrative only and are not intended to be limiting.

Other features and advantages of the disclosure will be apparent from the following detailed description and claims.

DETAILED DESCRIPTION

1. Compositions of the Present Disclosure

Figure 1A:
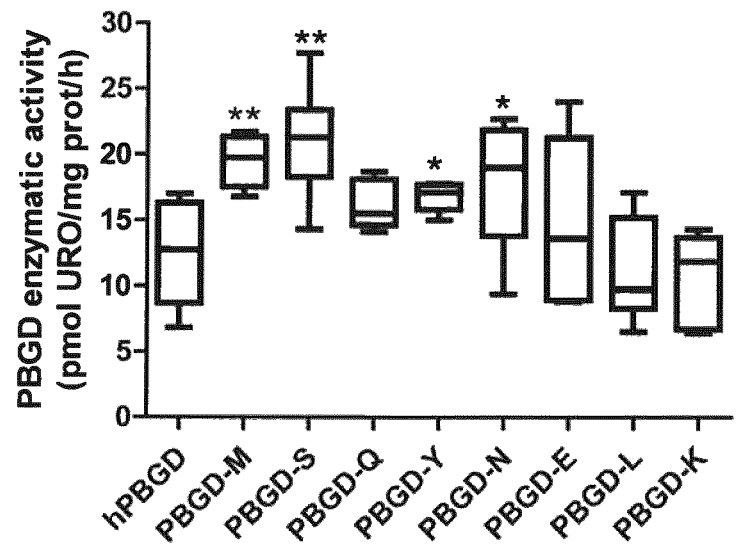
FIG. 1A is a graph showing the enzymatic activity of human housekeeping PBGD and various mutant variants when expressed in a prokaryotic system.

The present disclosure provides a modified human porphobilinogen deaminase (PBGD) protein having enhanced deaminase activity and comprising at least one amino acid mutation with respect to human housekeeping PBGD enzyme of SEQ ID NO:2. The modified PBGD can comprise at least two, at least three, at least four or at least five amino acid mutations.

The present disclosure also provides a modified human porphobilinogen deaminase (PBGD) protein having enhanced deaminase activity and comprising at least one amino acid mutation with respect to the human erythropoietic PBGD enzyme of SEQ ID NO:4. The modified PBGD can comprise at least two, at least three, at least four or at least five amino acid mutations.

In one aspect, the present disclosure provides a modified human PBGD protein, wherein the modified PBGD protein is a) a human non-erythropoietic housekeeping PBGD protein that comprises at least one amino acid mutation with respect to SEQ ID NO:2 selected from the group consisting of mutations N340S, I291M, H199Q, H120Y, and S344N; or b) a human erythropoietic PBGD protein that comprises at least one amino acid mutation with respect to SEQ ID NO:4 selected from the group consisting of mutations N323S, I274M, H182Q, H103Y, and S327N. The modified human non-erythropoietic housekeeping PBGD can comprise at least two, at least three, at least four or at least five amino acid mutations selected from N340S, I291M, H199Q, H120Y, and S344N. In one aspect, the modified PBGD protein comprises two of these amino acid mutations. The present disclosure also provides a modified human PBGD protein, wherein the modified PBGD protein is a) a human non-erythropoietic housekeeping PBGD protein that comprises at least one amino acid mutation with respect to the amino acid sequence set forth as SEQ ID NO:2 selected from the group consisting of mutations N340S, I291M, H199Q, H120Y, and S344N; or b) a human erythropoietic PBGD protein that comprises at least one amino acid mutation with respect to the amino acid sequence set forth as SEQ ID NO:4 selected from the group consisting of mutations N323S, I274M, H182Q, H103Y, and S327N. The present disclosure also provides a human porphobilinogen deaminase (PBGD) polypeptide comprising a) a human non-erythropoietic housekeeping porphobilinogen deaminase (PBGD) amino acid sequence as set forth in SEQ ID NO:2, comprising at least one amino acid mutation with respect to SEQ ID NO:2 selected from the group consisting of mutations N340S, I291M, H199Q, H120Y, and S344N; or b) a human erythropoietic PBGD amino acid sequence as set forth in SEQ ID NO:4, comprising at least one amino acid mutation with respect to SEQ ID NO 4 selected from the group consisting of mutations N323S, I274M, H182Q, H103Y, and S327N. In one aspect, the modified PBGD protein has enhanced or increased porphobilinogen deaminase activity. Enhanced or increased porphobilinogen deaminase activity may be determined by any means known in the art, for example, by assays such as those as described by Unzu et al. Mol Ther 2011; 19: 243-250 or Wright and Lim (1983, Biochem. J. 213: 85-88).

In one aspect, the present disclosure provides a polypeptide having at least 95%, at least 96%, at least 97%, at least 98%, or at least 99% identity to, and comprising at least one amino acid mutation with respect to a polypeptide having an amino acid sequence as set forth in SEQ ID NO:2 or SEQ ID NO:4. Percent identity can be determined by any means known in the art, for example the Needleman and Wunsch global alignment algorithm. In another aspect, the present disclosure provides a polypeptide having at least 95%, at least 96%, at least 97%, at least 98%, or at least 99% identity to, and comprising at least one amino acid mutation with respect to a polypeptide having an amino acid sequence as set forth in SEQ ID NO:2 or SEQ ID NO:4, wherein the polypeptide having the at least one amino acid mutation has increased deaminase activity when compared to the amino acid sequence of SEQ ID NO:2 or SEQ ID NO:4, respectively.

The present disclosure provides a modified human non-erythropoietic housekeeping PBGD protein that comprises the mutation N340S and at least one additional amino acid mutation selected from the group consisting of mutations I291M, H199Q, H120Y, and S344N with respect to SEQ ID NO:2.

In particular aspects, the present disclosure provides modified PBGD proteins: hkPBGD$_{[N340S]}$, hkPBGD$_{[I291M]}$, hkPBGD$_{[H199Q]}$, hkPBGD$_{[H120Y]}$, hkPBGD$_{[S344N]}$, hkPBGD$_{[N340S, I291M]}$, hkPBGD$_{[N340S, H199Q]}$, and hk PBGD$_{[N340S, H120Y]}$. The modified PBGD proteins can provide increased PBGD activity when compared with human housekeeping PBGD protein (hkPBGD) of SEQ ID NO:2.

In a preferred aspect, the modified human PBGD protein comprises the amino acid sequence of SEQ ID NO:6. SEQ ID NO:6 comprises the amino acid mutations N340S and I291M and is also referred to as hkPBGD$_{[N340S, I291M]}$ or hkPBGD$_{SM}$. As described herein, the modified human PBGD protein comprising the amino acid sequence of SEQ ID NO:6 surprisingly provides significantly higher catalytic activity than that of modified PBGD proteins comprising one of the mutations N340S, I291M, H199Q, H120Y, or S344N.

The present disclosure provides a modified human PBGD protein having enhanced deaminase activity and comprising at least one amino acid mutation with respect to human housekeeping PBGD enzyme of SEQ ID NO:2, wherein the modified PBGD protein is conjugated to at least one carrier polypeptide or a functionally equivalent variant thereof. The modified PBGD conjugated to at least one carrier polypeptide can comprise at least two, at least three, at least four or at least five amino acid mutations.

The present disclosure also provides a modified human PBGD protein having enhanced deaminase activity and comprising at least one amino acid mutation with respect to the human erythropoietic PBGD enzyme of SEQ ID NO:4, wherein the modified PBGD protein is conjugated to at least one carrier polypeptide or a functionally equivalent variant thereof. The modified PBGD conjugated to at least one carrier polypeptide can comprise at least two, at least three, at least four or at least five amino acid mutations.

In one aspect the present disclosure provides a modified human PBGD protein, wherein the modified PBGD protein is a) a human non-erythropoietic housekeeping PBGD protein that comprises at least one amino acid mutation with respect to SEQ ID NO:2 selected from the group consisting of mutations N340S, I291M, H199Q, H120Y, and S344N, wherein the modified PBGD protein is conjugated to at least one carrier polypeptide, or a functionally equivalent variant thereof; or b) a human erythropoietic PBGD protein that comprises at least one amino acid mutation with respect to SEQ ID NO:4 selected from the group consisting of mutations N323S, I274M, H182Q, H103Y, and S327N, wherein the modified PBGD protein is conjugated to at least one carrier polypeptide or a functionally equivalent variant thereof. In one aspect, the modified PBGD protein has enhanced or increased porphobilinogen deaminase activity.

The modified human PBGD protein and the carrier polypeptide, or a functionally equivalent variant thereof, can be covalently or non-covalently bound. In a preferred aspect, the modified human PBGD protein and the carrier polypeptide, or a functionally equivalent variant thereof, are covalently bound. The modified human PBGD protein and the carrier polypeptide, or a functionally equivalent variant thereof can form a single polypeptide chain. The C-terminal end of carrier polypeptide can be bound to the N-terminal end of the modified human PBGD protein or the N-terminal end of carrier polypeptide can be bound to the C-terminal end of modified human PBGD protein. In a preferred aspect, the C-terminal end of carrier polypeptide is bound to the N-terminal end of modified human PBGD protein. The conjugated modified PBGD protein can further optionally comprise other functional elements, including but not limited to, purification tags, affinity moieties, or linker polypeptides connecting PBGD protein to carrier polypeptide. Suitable linker elements and methods of producing the modified human PBGD protein and the carrier polypeptide conjugate molecules provided herein are described in U.S. Patent Publication No. 2016/0074475.

In one aspect, the carrier polypeptide is an Apo A molecule, an Apo E molecule, an Albumin molecule, or the constant fraction Fc of an immunoglobulin molecule, or a functionally equivalent variant thereof.

In the context of the present disclosure, "Apo A protein" or "Apo A molecule" is understood as any member of the Apo A family forming part of the high-density lipoproteins (HDLs) and which is capable of interacting specifically with receptors on the surface of liver cells, thus ensuring its capacity to carry the molecules of interest coupled to said Apo A protein to this organ. The Apo A molecules which can be used in the present disclosure are selected from the group of ApoA-I, ApoA-II, ApoA-III, ApoA-IV and ApoA-V, or functionally equivalent variants thereof.

In a specific aspect, the Apo A protein is the ApoA-I protein. ApoA-I is understood as the mature form of the pre-proApoA-I protein forming part of the high-density lipoproteins (HDLs). ApoA-I is synthesized as a precursor (pre-proApoA-I) containing a secretion signal sequence which is eliminated to give rise to the precursor. The signal sequence is made up of 18 amino acids, the propeptide of 6 amino acids and the mature form of the protein of 243 amino acids. The mature form of the protein which lacks a signal peptide and is processed is preferably used. In one preferred aspect, ApoA-I comprises the amino acid sequence of SEQ ID NO:7.

A functionally equivalent variant of ApoA-I is understood as all those polypeptides resulting from the insertion, substitution or deletion of one or more amino acids of the previously mentioned human or murine ApoA-I sequence and substantially maintaining intact the capacity to interact with the so-called "scavenger receptor class B type I" (SR—BI) forming the HDL receptor present in liver cells. The capacity to interact with the HDL receptor is determined essentially as has been described by Monaco et al (EMBO J., 1987, 6:3253-3260) by means of studies of ApoA-I binding to the hepatocyte membrane or by means of determining the capacity of ApoA-I or of its variant to inhibit the binding of HDL to the hepatocyte membrane receptors. The dissociation constant of the binding of the variant of ApoA-I to the hepatocyte membranes is preferably at least $10^{-8}$ M, $10^{-7}$ M, $10^{-6}$ M, $10^{-5}$ M or $10^{-4}$ M.

Variants of ApoA-I contemplated in the context of the present disclosure include polypeptides showing at least 60%, 65%, 70%, 72%, 74%, 76%, 78%, 80%, 90%, 95% or 99% similarity or identity with the ApoA-I polypeptides. For example, variants of ApoA-I contemplated in the context of the present disclosure include polypeptides showing at least 60%, 65%, 70%, 72%, 74%, 76%, 78%, 80%, 90%, 95% or 99% similarity to human ApoA-I of SEQ ID NO:7 or to mouse ApoA-1 (UniProt Accession #Q00623-1). The degree of identity between two polypeptides is determined using computer algorithms and methods that are widely known by persons skilled in the art. The identity between two amino acid sequences is preferably determined using the BLASTP algorithm (BLAST Manual, Altschul, S. et al., NCBI NLM NIH Bethesda, Md. 20894, Altschul, S., et al., J., 1990, Mol. Biol. 215:403-410).

The variants of ApoA-I used in the context of the disclosure preferably have a long serum half-life with respect to native ApoA-I, which allows reaching serum ApoA-I levels greater than those observed with ApoA-I. Methods for determining the serum half-life of a protein and, in particular of ApoA-I, are known in the art and include, among others, using the methods based on metabolic labeling with labeled proteins described by Eisenberg, S. et al (J. Lipid Res., 1973, 14:446-458), by Blum et al. (J. Clin. Invest., 1977, 60:795-807) and by Graversen et al (J Cardiovasc Pharmacol., 2008, 51:170-177). An example of said variants which shows a longer half-life is, for example, the variant called Milano (which contains the mutation R173C).

The carrier polypeptide, such as an ApoA-I protein, can improve the pharmacokinetic properties of the modified PBGD protein when compared to the unconjugated modified PBGD protein. In certain aspects, the conjugated modified PBGD protein has increased half-life, increased catalytic activity, increased serum stability and/or promotes protein translocation to the liver, when compared to the unconjugated modified PBGD protein or compared to unmodified human housekeeping PBGD.

In certain aspects, a modified PBGD protein of the present disclosure conjugated to a carrier polypeptide, such as an ApoA-I protein, confers surprisingly advantageous therapeutic properties to the conjugated modified PBGD protein, including but not limited to: ability to metabolize serum PBG; ability to cross the blood-brain barrier; and/or ability to target the liver. The ability to metabolize serum PBG can ensure quick (minutes) and long-lasting (up to five days) action. The ability to cross the blood-brain barrier permits the detoxification of PBG metabolites accumulated in the central nervous system. The ability to target the liver can extend the protection against acute AIP attacks for up to one month.

The present disclosure provides modified human PBGD protein conjugated to ApoA-I as a carrier polypeptide. In one aspect, the present disclosure provides modified ApoAI-PBGD$_{[N340S, I291M]}$ and/or modified PBGD$_{[N340S, I291M]}$-ApoAI. In a preferred aspect, the ApoAI-PBGD$_{[N340S, I291M]}$ has the amino acid sequence of SEQ ID NO:13. In a particular aspect, modified ApoAI-PBGD$_{[N340S, I291M]}$ surprisingly demonstrates increased catalytic activity when compared to the catalytic activity of PBGD$_{[N340S, I291M]}$-ApoAI, ApoAI-PBGD, and/or PBGD-ApoAI. The conjugated modified PBGD proteins of the present disclosure are suitable for administration to a subject in need thereof. In particular aspects, the conjugated modified PBGD proteins of the present disclosure are suitable for subcutaneous and/or intravenous administration. A detailed description of the conjugation of an ApoA molecule and a therapeutic protein is provided in U.S. Patent Publication No. 2016/0074475 and PCT Publication No. WO2009150284.

The present disclosure provides a polynucleotide comprising a nucleic acid sequence encoding a modified human PBGD protein as described herein. The present disclosure provides a polynucleotide comprising a nucleic acid sequence encoding a modified human PBGD protein having enhanced deaminase activity and comprising at least one amino acid mutation with respect to human housekeeping PBGD enzyme of SEQ ID NO:2. The polynucleotide comprising a nucleic acid sequence can encode a modified PBGD protein comprising at least two, at least three, at least four or at least five amino acid mutations.

The present disclosure also provides a polynucleotide comprising a nucleic acid sequence encoding a modified human PBGD protein having enhanced deaminase activity and comprising at least one amino acid mutation with respect to human erythropoietic PBGD enzyme of SEQ ID NO:4. The polynucleotide comprising a nucleic acid sequence can encode a modified PBGD protein comprising at least two, at least three, at least four or at least five amino acid mutations.

The present disclosure provides a polynucleotide comprising a nucleic acid sequence encoding a modified human PBGD protein, wherein the modified PBGD protein is a) a human non-erythropoietic housekeeping PBGD protein that comprises at least one amino acid mutation with respect to SEQ ID NO:2 selected from the group consisting of mutations N340S, I291M, H199Q, H120Y, and S344N; or b) a human erythropoietic PBGD protein that comprises at least one amino acid mutation with respect to SEQ ID NO:4 selected from the group consisting of mutations N323S, I274M, H182Q, H103Y, and S327N. In one aspect, the encoded modified PBGD protein has enhanced or increased porphobilinogen deaminase activity.

In one aspect, the present disclosure provides a polynucleotide comprising a nucleic acid sequence wherein a) at least 320 of the codons encoding modified human PBGD protein are identical to the codons of the housekeeping codon optimized sequence of SEQ ID NO:1; or b) at least 305 of the codons encoding modified human PBGD protein are identical to the codons of the erythroid codon optimized sequence of SEQ.ID.NO.3. Codon optimized PBGD SEQ ID NO:1 which encodes human housekeeping PBGD is described in further detail in PCT Publication Nos. WO2010036118 and WO2016037931 and U.S. Pat. No. 8,697,665. In one aspect, the present disclosure provides a polynucleotide comprising a nucleic acid sequence wherein a) the coding sequence is at least 95%, at least 96%, at least 97%, at least 98%, or at least 99% identical over its entire length to SEQ ID NO:1, or b) the coding sequence is at least 95%, at least 96%, at least 97%, at least 98%, or at least 99% identical over its entire length to the sequence SEQ ID NO:3, which percent identity is determined by the Needleman and Wunsch global alignment algorithm.

The nucleic acid sequence coding for a modified human PBGD can be a synthetic nucleotide sequence. The term "synthetic nucleotide sequence" is herein understood to mean that the nucleotide sequence does not occur as such in nature, but rather was designed, engineered and/or constructed by human intervention. The term "synthetic" thus does not necessarily imply that the sequence is exclusively and/or entirely obtained through chemical synthesis. Rather, although parts of the synthetic sequence may at one stage have been obtained through chemical synthesis, molecules comprising a synthetic sequence of the disclosure will usually be obtained from biological sources such as cultured cells, for example, recombinant cells.

To encode a modified human PBGD protein of the present disclosure, the polynucleotide must comprise at least one modified codon with respect to SEQ ID NO:1 or SEQ ID NO:3 such that it encodes at least one mutated amino acid. Non-limiting examples of mutations in hkPBGD proteins and polynucleotides are summarized in Table 1.

TABLE 1

| Modified PBGD Protein | Amino acid mutation | Original codon | Bases mutations | Mutated codon |
|---|---|---|---|---|
| hkPBGD$_{[N340S]}$ | N340S | aac | 1019A > G | 1018 . . . 1020: agc |
| hkPBGD$_{[I291M]}$ | I291M | atc | 873C > G | 871 . . . 873: atg |
| hkPBGD$_{[H199Q]}$ | H199Q | cac | 597C > G | 595 . . . 597: cag |
| hkPBGD$_{[H120Y]}$ | H120Y | cac | 358C > T | 358 . . . 360: tac |
| hkPBGD$_{[S344N]}$ | S344N | tcc | 1030T > A & 1031C > A | 1030 . . . 1032: aac |
| . . . | . . . | | | |
| hkPBGD$_{[S45L]}$ | S45L | tcc | 133T > C, 134C > T & 135C > G | 133 . . . 135: ctg |
| hkPBGD$_{[R164K]}$ | R164K | cgg | 490C > A & 491G > A | 490 . . . 492: aag |
| hkPBGD$_{[Q332E]}$ | Q332E | cag | 994C > G | 994 . . . 996: gag |

Amino acid mutation is referred by the position of the amino acid with respect to human housekeeping PBGD [hkPBGD] (SEQ ID NO:2). Original codon refers to the codon for the particular amino acid in codon optimized SEQ ID NO:1. The last three modified PBGD proteins in Table 1 did not show a significant enhancement of catalytic activity.

Non-limiting examples of mutations in human erythroid PBGD proteins and polynucleotides are summarized in Table 2.

TABLE 2

| Modified PBGD Protein | Amino acid mutation | Original codon | Bases mutations | Mutated codon |
|---|---|---|---|---|
| ePBGD$_{[N323S]}$ | N323S | aac | 968A > G | 967 . . . 969: agc |
| ePBGD$_{[I274M]}$ | I274M | atc | 822C > G | 820 . . . 822: atg |
| ePBGD$_{[H182Q]}$ | H182Q | cac | 546C > G | 544 . . . 546: cag |
| ePBGD$_{[H103Y]}$ | H103Y | cac | 307C > T | 307 . . . 309: tac |
| ePBGD$_{[S327N]}$ | S327N | tcc | 979T > A & 980C > A | 979 . . . 981: aac |
| . . . | . . . | | | |
| ePBGD$_{[S28L]}$ | S28L | tcc | 81T > C, 82C > T & 84C > G | 82 . . . 84: ctg |
| ePBGD$_{[R147K]}$ | R147K | cgg | 439C > A & 440G > A | 439 . . . 441: aag |
| ePBGD$_{[Q315E]}$ | Q315E | cag | 943C > G | 943 . . . 945: gag |

Amino acid mutation is referred by the position of the amino acid with respect to human erythroid PBGD [ePBGD] (SEQ ID NO:4). Original codon refers to the codon for the particular amino acid in codon optimized SEQ ID NO:3 which encodes human erythroid PBGD.

The present disclosure provides a polynucleotide comprising a nucleic acid sequence comprising a) at least one base mutation with respect to SEQ ID NO:1 selected from the group consisting of 1019A>G, which results in mutated codon 1018 . . . 1020: agc, 873C>G, which results in mutated codon 871 . . . 873: atg, 597C>G, which results in mutated codon 595 . . . 597: cag, 358C>T, which results in mutated codon 358 . . . 360: tac; and 1030T>A and 1031C>A, which result in a mutated codon1030 . . . 1032: aac; or b) at least one base mutation with respect to SEQ ID NO:3 selected from the group consisting of 968A>G, which results in mutated codon 967 . . . 969: agc, 822C>G, which results in mutated codon 820 . . . 822: atg, 546C>G, which results in mutated codon 544 . . . 546: cag, 307C>T, which results in mutated codon 307 . . . 309: tac; and 979T>A and 980C>A, which result in a mutated codon 979 . . . 981: aac.

In one aspect, the polynucleotide comprises a nucleic acid sequence that encodes modified human PBGD protein selected from the group consisting of SEQ ID NO:5 (encodes PBGD$_{[N340S, I291M]}$ of SEQ ID NO:6) and SEQ ID NO:12 (encodes conjugate of human ApoA-I with PBGD$_{[N340S, I291M]}$ of SEQ ID NO:13).

The polynucleotide that comprises a nucleic acid sequence that encodes a modified human PBGD protein can be DNA or RNA. In one aspect, the polynucleotide is RNA. In a particular aspect, the polynucleotide has the structure of mRNA. In a particular aspect, the mRNA can be modified. Modifications of mRNA nucleic acids are described in further detail in U.S. Patent Publication Nos. US20140206752 and US20150086614 and US20160304552 and PCT Publication Nos. WO2016011226, WO2016014846, and WO2016011306.

Depending on the proposed use or therapeutic strategy of choice, the polynucleotide of the disclosure will include nucleotide sequences of other optional functional elements that are suitable for the particular option.

The polynucleotide that comprises a nucleic acid sequence that encodes a modified human PBGD protein can further comprise a nucleic acid sequence that encodes a signal peptide. The polynucleotide comprising a nucleic acid sequence encoding a modified human PBGD protein can further comprise a nucleic acid sequence that encodes a poly-A tail.

The polynucleotide comprising a nucleic acid sequence encoding a modified human PBGD protein can further comprise at least one of the following features: a) at least one 5' cap structure; b) a 5'-UTR; or c) a 3'-UTR. In one aspect, the polynucleotide further comprises two of the features. In one aspect, the polynucleotide can further comprise all three of these features.

The polynucleotides described herein may have different uses: among others, it may be used for the recombinant manufacture of modified human PBGD protein; to generate a viral vector for gene therapy; to generate a non-viral vector also for gene therapy, such as a polynucleotide with mRNA structure. A more complete description of viral vectors for gene therapy is provided in PCT Publication Nos. WO2016037931 and WO2016097219.

The present disclosure also provides a nucleic acid construct or a vector comprising a polynucleotide sequence comprising a nucleic acid sequence encoding a modified human PBGD protein. The vector can further comprise additional elements or features to permit the modified human PBGD protein encoded by the nucleic acid sequence to be expressed in a tissue or cell of interest.

The nucleic acid construct comprises a nucleic acid sequence of the disclosure as described herein. In the nucleic acid construct the nucleic acid sequence encoding the modified human PBGD of the present disclosure can be operably linked to a mammalian cell-compatible expression control sequence, e.g., a promoter. Many such promoters are known in the art (see Sambrook and Russell. Molecular cloning: a laboratory Manual; Third Edition; 2001 Cold Spring Harbor Laboratory Press). Constitutive promoters that are broadly expressed in many cell types, such as the CMV promoter may be used. However, promoters that are inducible, tissue-specific, cell-type-specific, or cell cycle-specific may be preferred. In one aspect, the nucleic acid sequence is operably linked to a liver-specific promoter. In a construct of the disclosure an expression control sequence for liver-specific expression is e.g. selected from the group consisting of an al-anti-trypsin (AAT) promoter, a thyroid hormone-binding globulin promoter, an albumin promoter, a thyroxin-binding globulin (TBG) promoter, an Hepatic Control Region (HCR)-ApoCII hybrid promoter, an HCR-hAAT hybrid promoter, an AAT promoter combined with the mouse albumin gene enhancer (Ealb) element and an apolipoprotein E promoter. Other examples include the E2F promoter for tumor-selective, and, in particular, neurological cell tumor-selective expression (Parr et al., 1997, Nat. Med. 3:1145-9) or the IL-2 promoter for use in mononuclear blood cells (Hagenbaugh et al., 1997, J Exp Med; 185: 2101-10). In a specific aspect, the promoter comprises the nucleic acid sequence of SEQ ID NO:8.

The polynucleotide comprising a nucleic acid sequence encoding a modified human PBGD protein can further comprise 1, 2 or 3 copies of a nucleotide sequence of an ALAS1 Drug-Responsive Enhancing Sequence (ADRES). The polynucleotide can comprise two tandem repeats of ADRES. In a specific aspect, the enhancer sequence comprises the nucleic acid sequence of SEQ ID NO:9. Use of ADRES elements in the context of viral vectors for gene therapy of acute porphyrias is described in PCT Publication No. WO2016037931.

The vector of the present disclosure can be a viral vector. The viral vector can be an adeno-associated viral vector, an adenoviral vector, or a lentiviral vector.

In one aspect, the viral vector is an adeno-associated viral (AAV) vector. In a particular aspect, the vector comprises 5'ITR and 3'ITR of an adeno-associated virus of AAV2, AAV1, or AAV4 serotype. In a specific aspect, the 5'ITR sequence comprises the nucleic acid sequence of SEQ ID NO:10 and 3'ITR sequence comprises the nucleic acid sequence of SEQ ID NO:11. Adeno-associated viral vectors are described in detail in U.S. Pat. No. 8,697,665.

The viral vector can be an adenoviral vector that comprises 5'ITR, ψ packaging signal, and 3'ITR of an adenovirus of Ad2 or Ad5 serotype. In one aspect, the adenovirus is a gutless or high-capacity adenovirus. In particular aspects, a viral vector for gene therapy comprises AAV vector comprising $PBGD_{[N340S,\ I291M]}$ or a high capacity or gutless adenoviral vector comprising $PBGD_{[N340S,\ I291M]}$. The viral vectors can be suitable for administration to a subject in need thereof. In a specific aspect, the viral vectors are suitable for intraarterial or intravenous administration.

The vector of the present disclosure can be a non-viral vector. The non-viral vector can comprise a polynucleotide of the disclosure with mRNA structure. In particular aspects, a non-viral vector comprises mRNA encoding $PBGD_{[N340S,\ I291M]}$, mRNA encoding ApoAI-$PBGD_{[N340S,\ I291M]}$ or mRNA encoding SignalPeptide-ApoAI-$PBGD_{[N340S,\ I291M]}$. The non-viral vectors can be suitable for administration to a subject in need thereof. In a specific aspect, the non-viral vectors are suitable for subcutaneous, muscular or intravenous administration.

The present disclosure also provides a viral particle comprising a polynucleotide sequence comprising nucleic acid construct or vector comprising a nucleic acid sequence encoding a modified human PBGD protein. The viral particle can further comprise additional elements or features to permit the modified human PBGD protein encoded by the nucleic acid sequence to be expressed in a tissue or cell of interest.

The terms "viral particle", and "virion" are used herein interchangeably and relate to an infectious and typically replication-defective virus particle comprising the viral genome (i.e. the nucleic acid construct of the expression viral vector) packaged within a capsid and, as the case may be, a lipidic envelope surrounding the capsid.

In one aspect, optionally in combination with one or more features described herein, the viron is a "recombinant AAV virion" or "rAAV virion" obtained by packaging of a nucleic acid construct of an AAV vector according to the disclosure in a protein shell. Proteins of the viral capsid of an adeno-associated virus (capsid proteins VP1, VP2, and VP3) are generated from a single viral gene (cap gene). Differences among the capsid protein sequences of the various AAV serotypes result in the use of different cell surface receptors for cell entry. In combination with alternative intracellular processing pathways, this gives rise to distinct tissue tropisms for each AAV serotype.

In a particular aspect, a recombinant AAV virion according to the disclosure may be prepared by encapsidating the nucleic acid construct of an AAV genome derived from a particular AAV serotype on a viral particle formed by natural Cap proteins corresponding to an AAV of the same particular serotype. Nevertheless, several techniques have been developed to modify and improve the structural and functional properties of naturally occurring AAV viral particles (Biinning H et al. J Gene Med 2008; 10: 717-733). Thus, in another AAV viral particle according to the disclosure the nucleotide construct of the viral vector flanked by ITR(s) of a given AAV serotype can be packaged, for example, into: a) a viral particle constituted of capsid proteins derived from a same or different AAV serotype [e.g. AAV2 ITRs and AAV5 capsid proteins; AAV2 ITRs and AAV8 capsid proteins; etc]; b) a mosaic viral particle constituted of a mixture of capsid proteins from different AAV serotypes or mutants [e.g. AAV2 ITRs with AAV1 and AAV5 capsid proteins]; c) a chimeric viral particle constituted of capsid proteins that have been truncated by domain swapping between different AAV serotypes or variants [e.g. AAV2 ITRs with AAV5 capsid proteins w ith AAV3 domains]; or d) a targeted viral particle engineered to display selective binding domains, enabling stringent interaction with target cell specific receptors [e.g. AAV4 ITRs with AAV2 capsid proteins genetically truncated by insertion of a peptide ligand; or AAV2 capsid proteins non-genetically modified by coupling of a peptide ligand to the capsid surface].

The skilled person will appreciate that the AAV virion according to the disclosure may comprise capsid proteins of any AAV serotype. In one aspect, optionally in combination with one or more features described herein, the viral particle comprises capsid proteins of an AAV. In a particular aspect, optionally in combination with one or more features described herein, the AAV viral particle comprises capsid proteins from a serotype selected from the group consisting of an AAV 1, an AAV5, an AAV7, an AAV8, and an AAV9 which are more suitable for delivery to the liver cells (Nathwani et al. Blood 2007; 109: 1414 1421; Kitajima et al. Atherosclerosis 2006; 186:65-73). In a particular aspect, optionally in combination with one or more features disclosed herein, the viral particle comprises a nucleic acid construct of the invention wherein the 5 'ITR and 3 'ITR sequences of the nucleic acid construct are of an AAV2 serotype and the capsid proteins are of an AAV8 serotype. In a particular aspect, the AAV viral particle comprises at least a capsid protein from Anc80, a predicted ancestor of viral AAVs serotypes 1, 2, 8, and 9 that behaves as a highly potent gene therapy vector for targeting liver, muscle and retina (Zinn et al. Cell Reports 2015; 12: 11). In a more particular aspect, the viral particle comprises the Anc80L65 VP3 capsid protein (Genbank accession number: KT235804).

Viral particles, and methods of producing viral particles, are described in detail in PCT Publication Nos. WO2016/097218 and WO2016/037931.

A "nucleic acid" includes any molecule composed of or comprising monomeric nucleotides. The term "nucleotide sequence" may be used interchangeably with "nucleic acid" herein. A nucleic acid may be an oligonucleotide or a polynucleotide. A nucleic acid may be a DNA or an RNA. A nucleic acid may be chemically modified or artificial. Artificial nucleic acids include peptide nucleic acid (PNA), Morpholino and locked nucleic acid (LNA), as well as glycol nucleic acid (GNA) and threose nucleic acid (TNA). Each of these is distinguished from naturally-occurring DNA or RNA by changes to the backbone of the molecule. Also, phosphorothioate nucleotides may be used. Other deoxynucleotide analogs include methylphosphonates, phosphoramidates, phosphorodithioates, N3'P5'-phosphoramidates and oligoribonucleotide phosphorothioates and their 2'-0-allyl analogs and 2'-0-methylribonucleotide methylphosphonates which may be used in a nucleic acid of the disclosure.

A "nucleic acid construct" is herein understood to mean a man-made nucleic acid molecule resulting from the use of recombinant DNA technology. A nucleic acid construct is a nucleic acid molecule, either single- or double-stranded, which has been modified to contain segments of nucleic acids, which are combined and juxtaposed in a manner, which would not otherwise exist in nature. A nucleic acid construct usually is a "vector", i.e. a nucleic acid molecule which is used to deliver exogenously created DNA into a host cell.

One type of nucleic acid construct is an "expression cassette" or "expression vector". These terms refer to nucleotide sequences that are capable of effecting expression of a gene in host cells or host organisms compatible with such sequences. Expression cassettes or expression vectors typically include at least suitable transcription regulatory sequences and optionally, 3' transcription termination signals. Additional factors necessary or helpful in effecting expression may also be present, such as expression enhancer elements.

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species. The term "heterologous" may be used to indicate that in nature the nucleic acid or polypeptide molecule is produced by a host cell or organisms of a different species.

As used herein, the term "operably linked" refers to a linkage of polynucleotide (or polypeptide) elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

"Expression control sequence" refers to a nucleic acid sequence that regulates the expression of a nucleotide sequence to which it is operably linked. An expression control sequence is "operably linked" to a nucleotide sequence when the expression control sequence controls and regulates the transcription and/or the translation of the nucleotide sequence. Thus, an expression control sequence can include promoters, enhancers, internal ribosome entry sites (IRES), transcription terminators, a start codon in front of a protein-encoding gene, splicing signals for introns, and stop codons. The term "expression control sequence" is intended to include, at a minimum, a sequence whose presence are designed to influence expression, and can also include additional advantageous components. For example, leader sequences and fusion partner sequences are expression control sequences. The term can also include the design of the nucleic acid sequence such that undesirable, potential initiation codons in and out of frame, are removed from the sequence. It can also include the design of the nucleic acid sequence such that undesirable potential splice sites are removed. It includes sequences or polyadenylation sequences (pA) which direct the addition of a polyA tail, i.e., a string of adenine residues at the 3'-end of mRNA, which may be referred to as polyA sequences. It also can be designed to enhance mRNA stability. Expression control sequences which affect the transcription and translation stability, e.g., promoters, as well as sequences which effect the translation, e.g., Kozak sequences, suitable for use in insect cells are well known to those skilled in the art. Expression control sequences can be of such nature as to modulate the nucleotide sequence to which it is operably linked such that lower expression levels or higher expression levels are achieved.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter, including e.g. attenuators or enhancers, but also silencers. A "constitutive" promoter is a promoter that is active in most tissues under most physiological and developmental conditions. An "inducible" promoter is a promoter that is physiologically or developmentally regulated, e.g. by the application of a chemical inducer. A "tissue specific" promoter is only active in specific types of tissues or cells.

A "3' UTR" or "3' non-translated sequence" (also often referred to as 3' untranslated region or 3'end) refers to the nucleic acid sequence found downstream of the coding sequence of a gene, which comprises, for example, a transcription termination site and (in most, but not all eukaryotic mRNAs) a polyadenylation signal. After termination of transcription, the mRNA transcript may be cleaved downstream of the polyadenylation signal and a poly(A) tail may be added, which is involved in the transport of the mRNA to the cytoplasm (where translation takes place).

The terms "substantially identical", "substantial identity" or "essentially similar" or "essential similarity" means that two peptide or two nucleotide sequences, when optimally aligned, such as by the programs GAP or BESTFIT using default parameters, share at least a certain percentage of sequence identity as defined elsewhere herein. GAP uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). It is clear than when RNA sequences are said to be essentially similar or have a certain degree of sequence identity with DNA sequences, thymine (T) in the DNA sequence is considered equal to uracil (U) in the RNA sequence. Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA or the open-source software Emboss for Windows (current version 2.7.1-07). Alternatively, percent similarity or identity may be determined by searching against databases such as FASTA, BLAST, etc.

The present disclosure also provides a host cell comprising a modified human PBGD protein, a polynucleotide encoding a modified human PBGD protein, a nucleic acid construct or vector comprising a polynucleotide encoding a modified human PBGD protein as described herein. In a particular aspect for therapeutic use, host cells of the present disclosure will express and secrete modified PBGD that will travel and be captured by hepatic cells.

2. Pharmaceutical Compositions

The present disclosure also provides pharmaceutical or veterinary compositions comprising a modified human PBGD protein, comprising a polynucleotide encoding a modified human PBGD protein, comprising a nucleic acid construct or vector comprising a polynucleotide encoding a modified human PBGD protein or comprising a host cell as described in the instant disclosure; and a pharmaceutically or veterinary acceptable carrier or excipient.

As used herein, the phrase "pharmaceutically acceptable" or "veterinary acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

Any suitable pharmaceutically acceptable carrier or excipient can be used in the present compositions (See e.g., Remington: The Science and Practice of Pharmacy, Alfonso R. Gennaro (Editor) Mack Publishing Company, April 1997). This includes any and all solvents, dispersion media, coatings, antibacterial and antifungal agents, isotonic and absorption delaying agents, and the like that are physiologically compatible. Pharmaceutically acceptable carriers include sterile aqueous solutions or dispersions and sterile powders. The use of such media and agents for pharmaceutically active substances is well known in the art. Except insofar as any conventional media or agent is incompatible with the active compound, use thereof in the pharmaceutical compositions of the disclosure is contemplated. Preferred pharmaceutical forms would be in combination with sterile saline, dextrose solution, or buffered solution, or other pharmaceutically acceptable sterile fluids. Alternatively, a solid carrier may be used such as for example, microcarrier beads.

Pharmaceutical compositions are typically sterile and stable under the conditions of manufacture and storage. Pharmaceutical compositions may be formulated as a solution, microemulsion, liposome, or other ordered structure suitable to accommodate high drug concentration. The carrier may be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as a lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. The compounds or compositions of the present disclosure may be administered in a time or controlled release formulation, for example in a composition which includes a slow release polymer or other carriers that will protect the compound against rapid release, including implants and microencapsulated delivery systems. Biodegradable, biocompatible polymers may, for example, be used, such as ethylene vinyl acetate, polyanhydrides, polyglycolic acid, collagen, polyorthoesters, polylactic acid and polylactic, polyglycolic copolymers (PLG). Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

A pharmaceutical or veterinary composition of the disclosure is formulated to be compatible with its intended route of administration. Examples of routes of administration include parenteral, e.g., intravenous, intraarterial, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. For intravenous administration, suitable carriers include physiological saline, bacteriostatic water, Cremophor EL™ (BASF, Parsippany, N.J.) or phosphate buffered saline (PBS). The parenteral preparation can be enclosed in ampoules, disposable syringes or multiple dose vials made of glass or plastic.

The pharmaceutical compositions containing compositions of the present disclosure may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

The pharmaceutical compositions can be included in a container, pack, or dispenser together with instructions for administration.

3. Methods of Use

Acute intermittent porphyria (AIP) is an inherited metabolic disease characterized by a deficiency of porphobilinogen deaminase (PBGD), the third enzyme of the heme synthesis pathway. The enzyme activity is about 50% of normal in those who inherit the genetic trait. The disease is inherited in an autosomal dominant manner and is the most common of acute porphyrias. The dominant clinical feature is an acute intermittent attack due to dysfunction of the nervous system, including abdominal pain and neurovisceral and circulatory disturbances. Abdominal pain has been reported in 85-95% of cases and is the most common feature, followed by or associated with the neurological changes. Progression to respiratory and bulbar paralysis and death may occur if AIP is not recognized and harmful drugs are not withdrawn, such as drugs metabolized by the hepatic cytochrome P450 enzymes which may precipitate an attack. Sudden death may also occur as result of cardiac arrhythmia. Primary liver cancer and impaired renal function sometimes occur as well.

An inherited deficiency of PBGD is not enough for the symptoms to appear. A high proportion of subjects that inherit PBGD mutation never develop porphyric symptoms, i.e. there is very low clinical penetrance. Clinical symptoms in AIP carriers are associated with increased production and excretion of the porphyrin precursors δ-aminolevulinic acid (ALA) and porphobilinogen (PBG) as result of increased demand of hepatic heme synthesis due to a drug or other precipitating factors that provoke the acute attack. In these conditions, PBGD deficiency limits heme synthesis and as a result, heme-mediated repression of hepatic ALA synthase (ALAS1) is impaired. There is evidence indicating that the liver is the main source of the excess of porphyrin precursors. These compounds remain elevated between attacks in those subjects prone to repeated porphyric crises and increase further during the crisis. They may decrease to normal if the disease remains inactive for a long period of time.

Acute attacks usually occur after puberty and can be induced in latent individuals by endocrine factors and steroid hormones and a variety of environmental factors including drug, nutritional factors, restricted carbohydrate and caloric intake, smoking, steroid hormones and oral contraceptives, lead poisoning, intercurrent infections, surgery and psychological stress. Drugs are among the most important factors that precipitate acute attacks and a list of safe drugs is available in www.drugs-porphyria.com. Smoking, ethanol, and drugs metabolized by CYP450, greatly increase hepatic heme demand and result in the induction of ALAS1, which increases the production of porphyrin precursors and precipitates an acute attack. Also, ALAS1 is positively regulated by the peroxisome proliferator-activated receptor γ coactivator 1α (PGC1α), which is induced in the liver during fasting. Among the precipitating factors steroid hormones seem to play an important role. This concept is supported by the fact that the disease rarely manifests before puberty and that oral contraceptives can exacerbate attacks in some females with PBGD deficiency. Also, women (80%) are affected more often than men (20%).

Acute attacks are treated with infusions of glucose and hemin. Glucose appears to antagonize the ALAS1 induction mediated by PGC1α. Hemin restores the regulatory heme pool and suppresses hepatic ALAS1 induction. Some women develop premenstrual attacks which can be prevented by gonadotropin-releasing hormone (GnRH) analogs. Some patients exhibit recurrent acute attacks and significant, disabling neurological dysfunction. Advanced neurologic damage and subacute and chronic symptoms are generally unresponsive to heme therapy. This is a life-threatening condition that can be cured only by allogeneic liver transplantation that, in more than eleven patients to date, prevents the accumulation of neurotoxic ALA and PBG. Nevertheless, liver transplantation has limited availability of compatible donors, and a significant morbidity and mortality.

Recombinant human non-erythroid porphobilinogen deaminase has been administered to healthy subjects and asymptomatic porphobilinogen deaminase-deficient subjects with high concentrations of PBG in a clinical trial (Sardh et al. *Clin Pharmacokinet.* 2007; 46(4):335-349). Despite the fact that recombinant human PBGD therapy rapidly decreased the plasma level of PBG, it had no effect on the ALA level or the patients' acute symptoms. Unfortunately, this therapeutic strategy has not progressed towards a feasible treatment.

Gene-replacement therapy is a potential alternative to liver transplantation in these patients where the liver function is entirely normal except for the PBGD deficiency. The feasibility of gene delivery therapies aiming to correct the hepatic enzyme defect are being explored in experimental models of AIP (AIP mice). Several studies have reported the delivery of human PBGD by means of adenoviral and adeno-associated viral vectors. For the acute porphyrias, increasing hepatic PBGD activity enough to convert the massively accumulated ALA and PBG into porphyrins for the following conversion into heme is still necessary. Since the acute porphyrias are hepatic encephalopathy, it is required to prevent the hepatic accumulation and/or clear the circulation of the porphyrin precursors as quickly as possible. The fact that these precursors are readily taken up by cells is advantageous since it is not necessary to overexpress a wild-type version of PBGD (rPBGD) to most or to all the hepatocytes. In fact, previous studies suggest that a high expression of exogenous PBGD in about 10% of the hepatocytes should be enough to achieve clinical benefit because the hepatocytes over-expressing high amounts of PBGD could metabolize the heme precursors produced by non-transduced neighboring cells (Unzu C et al. Mol Ther. 2011; 19(2):243-50).

To date, there has only been one clinical trial with a viral vector delivering and expressing PBGD for gene therapy of AIP (D'Avola et al. *J Hepatol.* 2016 October; 65(4):776-783). The vector assayed, rAAV2/5-PBGD, was characterized by this main features: a) a codon optimized nucleotide sequence that b) encodes human housekeeping PBGD c) driven by a chimeric liver-specific EalbAAT (contains al antitrypsin promoter with regulatory sequences from the human albumin enhancer) c) engineered within an AAV2-serotype genomic elements, d) and finally packaged within an AAV5 serotype capsid (Unzu et al. *Mol Ther,* 2011; 19: 243-250). Codon optimized DNA sequence for human housekeeping PBGD was first disclosed in PCT Publication No. WO2010036118 and U.S. Pat. No. 8,697,665. Studies in AIP animal model had shown that gene delivery of PBGD to hepatocytes using rAAV2/5-PBGD prevents mice from suffering porphyria acute attacks. In phase I, open label, dose-escalation, multicenter clinical trial the administration of rAAV2/5-PBGD to patients with severe AIP showed that is safe but metabolic correction was not achieved at the doses tested.

The present disclosure provides a method of increasing porphobilinogen deaminase activity in a subject in need thereof by administering a therapeutically effective amount of a modified human PBGD protein, by administering a therapeutically effective amount of a polynucleotide encoding a modified human PBGD protein, by administering a therapeutically effective amount of a nucleic acid construct or vector comprising a polynucleotide encoding a modified human PBGD protein, by administering a therapeutically effective amount of a host cell comprising a modified human PBGD protein, comprising a polynucleotide encoding a modified human PBGD protein, or comprising a nucleic acid construct or vector comprising a polynucleotide encoding a modified human PBGD protein, or by administering a therapeutically effective amount of a pharmaceutical or veterinary composition comprising a modified human PBGD protein, comprising a polynucleotide encoding a modified human PBGD protein, comprising a nucleic acid construct or vector comprising a polynucleotide encoding a modified human PBGD protein or comprising a host cell as described in the instant disclosure.

The present disclosure also provides a modified human PBGD protein, a polynucleotide encoding a modified human PBGD protein, a nucleic acid construct or vector comprising a polynucleotide encoding a modified human PBGD protein, a host cell comprising a modified human PBGD protein, comprising a polynucleotide encoding a modified human PBGD protein, or comprising a nucleic acid construct or vector comprising a polynucleotide encoding a modified human PBGD protein, or a pharmaceutical or veterinary composition comprising a modified human PBGD protein, comprising a polynucleotide encoding a modified human PBGD protein, comprising a nucleic acid construct or vector comprising a polynucleotide encoding a modified human PBGD protein or comprising a host cell as described in the instant disclosure for use in medicine.

The present disclosure provides a method of treating or preventing, or ameliorating at least one symptom of, a condition associated with, or caused by, a deficiency in porphobilinogen deaminase in a subject in need thereof by administering a therapeutically effective amount of a modified human PBGD protein, by administering a therapeutically effective amount of a polynucleotide encoding a modified human PBGD protein, by administering a therapeutically effective amount of a nucleic acid construct or vector comprising a polynucleotide encoding a modified human PBGD protein, by administering a therapeutically effective amount of a host cell comprising a modified human PBGD protein, comprising a polynucleotide encoding a modified human PBGD protein, or comprising a nucleic acid construct or vector comprising a polynucleotide encoding a modified human PBGD protein, or by administering a therapeutically effective amount of a pharmaceutical or veterinary composition comprising a modified human PBGD protein, comprising a polynucleotide encoding a modified human PBGD protein, comprising a nucleic acid construct or vector comprising a polynucleotide encoding a modified human PBGD protein or comprising a host cell as described in the instant disclosure. The condition associated with, or caused by, a deficiency in porphobilinogen deaminase can be acute porphyria. The acute porphyria can be acute intermittent porphyria. Such treatment may alleviate, ameliorate or reduce the severity of one or more symptoms of acute intermittent porphyria, for example reducing the incidence or severity of an attack. For example, treatment according to the disclosure may alleviate, ameliorate or reduce the severity of dysfunction of the nervous system, abdominal pain, back pain, constipation, nausea, vomiting, water-electrolyte imbalance, rashes, blisters, cramping or muscle weakness, sensitivity to light, anxiety, blood in the urine, urinary retention, rapid heart rate, increased blood pressure, itching, mental confusion, hallucinations, seizures, or neurovisceral and/or circulatory disturbances.

The present disclosure also provides a modified human PBGD protein, provides a polynucleotide encoding a modified human PBGD protein, provides a nucleic acid construct or vector comprising a polynucleotide encoding a modified human PBGD protein, provides a host cell comprising a modified human PBGD protein, comprising a polynucleotide encoding a modified human PBGD protein, or comprising a nucleic acid construct or vector comprising a polynucleotide encoding a modified human PBGD protein, or provides a pharmaceutical or veterinary composition comprising a modified human PBGD protein, comprising a polynucleotide encoding a modified human PBGD protein, comprising a nucleic acid construct or vector comprising a polynucleotide encoding a modified human PBGD protein or comprising a host cell as described in the instant disclosure for use in the treatment or prevention of, or amelioration of at least one symptom, a condition associated with, or caused by, a deficiency in porphobilinogen deaminase. The condition associated with, or caused by, a deficiency in porphobilinogen deaminase can be acute porphyria. The acute porphyria can be acute intermittent porphyria. Such treatment may alleviate, ameliorate or reduce the severity of one or more symptoms of acute intermittent porphyria, for example reducing the incidence or severity of an attack. For example, treatment according to the disclosure may alleviate, ameliorate or reduce the severity of dysfunction of the nervous system, abdominal pain, back pain, constipation, nausea, vomiting, water-electrolyte imbalance, rashes, blisters, cramping or muscle weakness, sensitivity to light, anxiety, blood in the urine, urinary retention, rapid heart rate, increased blood pressure, itching, mental confusion, hallucinations, seizures, or neurovisceral and/or circulatory disturbances.

The present disclosure also provides the use of a modified human PBGD protein, use of a polynucleotide encoding a modified human PBGD protein, use of a nucleic acid construct or vector comprising a polynucleotide encoding a modified human PBGD protein, use of a host cell comprising a modified human PBGD protein, comprising a polynucleotide encoding a modified human PBGD protein, or comprising a nucleic acid construct or vector comprising a polynucleotide encoding a modified human PBGD protein, or use of a pharmaceutical or veterinary composition comprising a modified human PBGD protein, comprising a polynucleotide encoding a modified human PBGD protein, comprising a nucleic acid construct or vector comprising a polynucleotide encoding a modified human PBGD protein or comprising a host cell as described in the instant disclosure in the preparation of a pharmaceutical or veterinary composition for use in the treatment or prevention of, or amelioration of at least one symptom of, a condition associated with, or caused by, a deficiency in porphobilinogen deaminase. The condition associated with, or caused by, a deficiency in porphobilinogen deaminase can be acute porphyria. The acute porphyria can be acute intermittent porphyria. Such treatment may alleviate, ameliorate or reduce the severity of one or more symptoms of acute intermittent porphyria, for example reducing the incidence or severity of an attack. For example, treatment according to the disclosure may alleviate, ameliorate or reduce the severity of dysfunction of the nervous system, abdominal pain, back pain, constipation, nausea, vomiting, water-electrolyte imbalance, rashes, blisters, cramping or muscle weakness, sensitivity to light, anxiety, blood in the urine, urinary retention, rapid heart rate, increased blood pressure, itching, mental confusion, hallucinations, seizures, or neurovisceral and/or circulatory disturbances.

The present disclosure also provides a method for the delivery of a nucleotide sequence encoding a modified PBGD protein to a subject in need thereof comprising administering a nucleic acid, a nucleic acid construct, a viral vector or a non-viral vector to the subject under conditions that result in the expression of a modified PBGD protein at a level that provides a therapeutic effect in the subject.

The compositions of the present disclosure can be administered by any means known in the art. Non-limiting examples of routes of administration include parenteral, e.g., intravenous, intraarterial, intradermal, subcutaneous, oral (e.g., inhalation), transdermal (topical), and transmucosal administration. In a specific aspect, the compositions of the present disclosure are administered parenterally. In preferred aspects, the compositions of the present disclosure are administered via intravenous, intraarterial or subcutaneous administration. The compositions of the present disclosure may be administered to any tissue or the interstitial space of tissue. In some aspects, the tissue target may be specific, for example, liver tissue, or it may be a combination of several tissues, for example, the muscle and liver tissues. Exemplary tissue targets may include liver, skeletal muscle, heart muscle, adipose deposits, kidney, lung, vascular endothelium, epithelial and/or hematopoietic cells.

An "effective amount" includes a therapeutically effective amount or a prophylactically effective amount. A "therapeutically effective amount" refers to an amount effective, at dosages and for periods of time necessary, to achieve the desired therapeutic result, such as an increase in PBGD activity. A therapeutically effective amount of the compositions of the present disclosure may vary according to factors such as the disease state, age, sex, and weight of the individual, and the ability of the compositions to elicit a desired response in the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. Regimens for continuing therapy, including dose, formulation, and frequency may be guided by the initial response and clinical judgment. A therapeutically effective amount is also typically one in which any toxic or detrimental effects of the compositions of the present disclosure are outweighed by the therapeutically beneficial effects. A "prophylactically effective amount" refers to an amount effective, at dosages and for periods of time necessary, to achieve the desired prophylactic result, such as preventing or inhibiting various conditions, including a condition associated with a reduction in PBGD levels. A prophylactic dose may be used in subjects prior to or at an earlier stage of disease, and a prophylactically effective amount may be more or less than a therapeutically effective amount in some cases. For gene therapy vectors of the present disclosure, a range for therapeutically or prophylactically effective amounts of compositions of the present disclosure may be from $1\times10^{12}$ and $1\times10^{13}$ genome copy (gc)/kg, for example from $1\times10^{11}$ to $1\times10^{12}$ gc/kg. Dosage ranges set forth herein are exemplary only and do not limit the dosage ranges that may be selected by medical practitioners.

It may be advantageous to formulate pharmaceutical compositions in dosage unit form for ease of administration and uniformity of dosage. "Dosage unit form" as used herein refers to physically discrete units suited as unitary dosages for subjects to be treated; each unit containing a predetermined quantity of active compositions calculated to produce the desired therapeutic effect in association with the required pharmaceutical carrier. The specification for the dosage unit forms of the disclosure may be dictated by the unique characteristics of the active composition and the particular therapeutic effect to be achieved, and by the limitations inherent in the art of compounding such an active composition for the treatment of a condition in individuals.

As used herein, a "subject in need thereof" is a subject having decreased or reduced porphobilinogen deaminase activity or a subject having a condition associated with, or caused by, a deficiency in porphobilinogen deaminase, or a subject having an increased risk of developing decreased or reduced porphobilinogen deaminase activity or developing a condition associated with, or caused by, a deficiency in porphobilinogen deaminase relative to the population at large. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

As used herein, "monotherapy" refers to the administration of a single active or therapeutic composition to a subject in need thereof. Preferably, monotherapy will involve administration of a therapeutically effective amount of an active composition. For example, a monotherapy with one of the compositions of the present disclosure, or a pharmaceutically acceptable salt thereof, to a subject in need of treatment. Monotherapy may be contrasted with combination therapy, in which a combination of multiple active compositions is administered, preferably with each component of the combination present in a therapeutically effective amount. In one aspect, monotherapy with a composition of the present disclosure, or a pharmaceutically acceptable salt thereof, is more effective than combination therapy in inducing a desired biological effect.

As used herein, "combination therapy" or "co-therapy" includes the administration of a composition of the present disclosure, or a pharmaceutically acceptable salt thereof, and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may be, but generally is not, intended to encompass the administration of two or more of these therapeutic agents as part of separate monotherapy regimens that incidentally and arbitrarily result in the combinations of the present disclosure.

"Combination therapy" is intended to embrace administration of these therapeutic agents in a sequential manner, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The methods of the present disclosure further provide for the administration of a second therapeutic agent (in addition to a composition of the instant disclosure) including glucose and other carbohydrates, heme (such as Panhematin®), heme arginate (such as Normosang®) or a combination thereof.

As used herein, "treating" or "treat" describes the management and care of a patient for the purpose of combating a disease, condition, or disorder and includes the administration of a composition of the present disclosure, to alleviate the symptoms or complications of a disease, condition or disorder, or to eliminate the disease, condition or disorder.

A composition of the present disclosure can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In one aspect, the administration of the compositions of the disclosure leads to the elimination of a sign or symptom, however, elimination is not required. Effective dosages are expected to decrease the severity of a sign or symptom. For instance, a sign or symptom of a disorder, which can occur in multiple locations, is alleviated if the severity of the disorder is decreased within at least one of multiple locations.

As used herein the term "symptom" is defined as an indication of disease, illness, injury, or that something is not right in the body. Symptoms are felt or noticed by the individual experiencing the symptom, but may not easily be noticed by others. Others are defined as non-health-care professionals. As used herein the term "sign" is also defined as an indication that something is not right in the body. But signs are defined as things that can be seen by a doctor, nurse, or other healthcare professional.

Treating a disorder or condition of the present disclosure can result in an increase in average survival time of a population of treated subjects in comparison to a population receiving carrier alone, in comparison to a population of untreated subjects or in comparison to a population receiving monotherapy with a drug that is not a composition of the present disclosure. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active composition. An increase in average survival time of a population may also be measured, for example, by calculating for a population the average length of survival following completion of the first round of treatment with an active composition.

Treating a disorder or condition of the present disclosure can result in a decrease in the mortality rate of a population of treated subjects in comparison to a population receiving carrier alone, in comparison to a population of untreated subjects or in comparison to a population receiving monotherapy with a drug that is not a composition of the present disclosure. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active composition. A decrease in the mortality rate of a population may also be measured, for example, by calculating for a population the Generation of DNA constructs: Eight DNA constructs were generated which encoded mutated PBGD proteins characterized in that they incorporated a different single amino acid mutation: respectively S45L, H120Y, R164K, H199Q, I291M, Q332E, N340S or S344N. Mutated PBGD sequences derived from codon optimized SEQ.ID.NO.1 that encodes human housekeeping PBGD enzyme (SEQ.ID.NO.2, with Uniprot Accession No. P08397-1). Details of mutated DNA and protein sequences were as follows.

Table 3. Amino acid mutation is referred by the position of the amino acid with respect to human housekeeping PBGD [hkPBGD] (SEQ.ID.NO.2; original sequence). Original codon refers to the codon for the particular amino acid in codon optimized SEQ.ID.NO.1. Mutated codon is the resultant codon after introducing respective bases mutations.

TABLE 3

| Modified PBGD Protein | Amino acid mutation | Original codon | Bases mutations | Mutated codon |
| --- | --- | --- | --- | --- |
| hkPBGD$_{[S45L]}$ | S45L | tcc | 133T > C, 134C > T & 135C > G | 133 . . . 135: ctg |
| hkPBGD$_{[H120Y]}$ | H120Y | cac | 358C > T | 358 . . . 360: tac |
| hkPBGD$_{[R164K]}$ | R164K | cgg | 490C > A & 491G > A | 490 . . . 492: aag |
| hkPBGD$_{[H199Q]}$ | H199Q | cac | 597C > G | 595 . . . 597: cag |
| hkPBGD$_{[I291M]}$ | I291M | atc | 873C > G | 871 . . . 873: atg |
| hkPBGD$_{[Q332E]}$ | Q332E | cag | 994C > G | 994 . . . 996: gag |
| hkPBGD$_{[N340S]}$ | N340S | aac | 1019A > G | 1018 . . . 1020: agc |
| hkPBGD$_{[S344N]}$ | S344N | tcc | 1030T > A & 1031C > A | 1030 . . . 1032: aac | average number of disease-related deaths per unit time following completion of the first round of treatment with an active composition.

Treating a disorder or condition of the present disclosure can result in a decrease in the morbidity rate of a population of treated subjects in comparison to a population receiving carrier alone, in comparison to a population of untreated subjects or in comparison to a population receiving monotherapy with a drug that is not a composition of the present disclosure. Preferably, the morbidity rate is decreased by more than 2%; more preferably, by more than 5%; more preferably, by more than 10%; and most preferably, by more than 25%. A decrease in the morbidity rate of a population of treated subjects may be measured by any reproducible means. In some aspects, a decrease in morbidity includes a reduction in the use of other medications, such as pain killers, decreased hospitalization, ability to return to work, reduction in hepatocarcinoma, or reduction in renal failure.

4. Examples

Example 1. Catalytic Activity of PBGD Enzyme Expressed from DNA Plasmids Encoding Different Modified Human Housekeeping PBGD Proteins Different DNA constructions were synthesized incorporating a codon optimized DNA sequence that encoded a mutated human housekeeping PBGD protein in which specific amino acids are mutated. The mutated PBGD sequences were cloned into the pET16B vector and transformed into *E. coli*, BL21(DE31) pLysS strain. The expression of the protein was induced and the cell culture was centrifuged before analyzing the PBGD activity in the bacterial pellet. The catalytic activity was also assessed in a eukaryotic system: the DNA constructs were cloned into a pTRE vector and the plasmids were injected to several groups of mice by hydrodynamic injection for later analyzing PBGD catalytic activity.

Several additional DNA constructs were generated that encoded mutated PBGD incorporating 2 out of the 8 amino acid mutations listed above: hkPBGD$_{[N340S, I291M]}$, hkPBGD$_{[N340S, H120Y]}$, hkPBGD$_{[N340S, H199Q]}$, for plasmid generation and testing of catalytic activity.

Generation of plasmid vectors for testing in the prokaryotic system: The 8 bioengineered DNA constructs and the construct encoding human hkPBGD (as control) were cloned into the pET-16B expression vector (Novagen). The protein synthesis is driven by a T7 promoter, which is inducible by isopropyl ß-D-1-thiogalactopyranoside (IPTG). Then, each vector was transformed into *E. coli* BL21 (DE31) pLysS strain. The expression of the gene of interest was induced by supplementing the culture medium with IPTG 0.05M (Invitrogen). Three hours later, the enzymatic activity was measured in the bacterial pellet.

Generation of plasmid vectors for testing in the eukaryotic system: DNA constructs carrying mutated PBGD sequences were cloned into an expression vector with a eukaryotic promoter. pTRE-Tight vector (Clontech Laboratories, Inc, Germany) was used to clone all these constructions where the synthesis of the proteins was driven by chimeric liver-specific promoter EalbAAT (SEQ.ID.NO.8; Unzu et al. Mol Ther 2011; 19: 243-250) instead of its CMV promoter. Furthermore, the constructions also presented a polyA sequence from PBGD in order to increase the stability of the mRNA.

T1 homozygous mice, which were 6-8 weeks old and had ~55% of natural hepatic PBGD activity (HMB-synthase activity), were injected with the generated plasmids (25 µg) and a plasmid carrying the non-mutated hkPBGD sequence as a control, via hydrodynamic injections into their tail veins as previously described (Unzu et al. Journal of Hepatology. 2010; 52(3):417-24). In brief, mice were put under a heated cage. The plasmid was resuspended in a volume of saline equivalent to 10% of the mouse body weight. The entire amount was delivered at a constant speed, in 5-8 s. Thereafter, mice were sacrificed 6 days post-injection, their livers were isolated and rinsed in ice-cold phosphate buffered saline (PBS), and then divided into different pieces and stored depending on the future analysis.

Determination of enzymatic PBGD activity: Samples to analyze the PBGD activity, either bacterial pellets or liver samples, were stored at 4° C. and the PBGD activity measured fluorometrically in fresh samples according to methods known in the art, such as those described in Unzu et al. Mol Ther 2011; 19: 243-250 or Anderson and Desnick (J Biol Chem. 1980; 255(5):1993-1999).

Briefly, the liver sample was homogenized in lysis buffer (sodium phosphate buffer 1 mM pH 7.6, dithiothreitol (DTT) 1 mM, $Cl_2Mg$ 1 mM and 0.05% triton X-100) and centrifuged at 16,000 g for 20 minutes at 4° C. The protein of the supernatant was determined by Bradford (BioRad) using an albumin standard and 1 mg of total protein was used to determine the PBGD activity. The liver sample was incubated in incubation buffer (Tris-HCl 0.1M pH 8.1 and DTT 0.1 mM) and 250 nmol of PBG (LivChem GmbH&Co.) in 1,200 μL of total volume for one hour at 37° C. The enzymatic reaction was stopped with 175 μL of cold 40% trichloroacetic acid (TCA) (Sigma) and the formed uroporphyrinogen was oxidized to uroporphyrin after 30 minutes of light exposure. The concentration of uroporphyrins was determined by a spectrofluorometer (Perkin Elmer LS 50 B) with an excitation wavelength of 405 nm and an emission wavelength of 595 nm. PBGD activity was expressed in terms of pmol uroporphyrin/mg protein/h using appropriate standards.

Detection of plasmid DNA in liver samples: Samples for measurement of the plasmid DNA were frozen in liquid nitrogen until the extraction of DNA. The normalization of the hepatic PBGD activity in mice was performed by the quantification of plasmid DNA in the liver samples by a real-time quantitative polymerase chain reaction (qPCR) using CFX-96 Real-Time PCR Detection System (BioRad, Hercules, Calif.). Every analysis was performed using iQ SYBR Green Supermix (BioRad) and primers annealing with human PBGD cDNA (forward primer: 5'-gcctgcagttcgagatcatt-3', SEQ.ID.NO.14; reverse primer: 5'-aggtccttcaggctgt-3', SEQ.ID.NO.15; product length: 157 bp). PCR amplification was performed under the following conditions: one cycle of 3 min at 95° C.; followed by 35 cycles of 30 s at 95° C., 15 s at 60° C., 25 s at 72° C., and 10 s at 80° C. and 10 s at 85° C.; followed by a final extension cycle of 72° C. for 4 min. To confirm the amplification specificity a melting curve was generated immediately after the PCR, increasing the incubation temperature from 55 to 95° C.

All samples were analyzed in duplicate and the expression of the gene of interest was normalized by comparison with glyceraldehyde 3-phosphate dehydrogenase (GAPDH) as an internal control (forward primer: 5'-ccaaggtcatccatgacaac-3', SEQ.ID.NO.16; reverse primer: 5'-tgtcataccaggaaatgagc-3', SEQ.ID.NO.17; product length: 682 bp). The quantification of the PCR product was expressed according to the formula $2^{Ct(GAPDH)-Ct(PBGD)}$, where Ct is the cycle at which fluorescence from amplification exceeds the background fluorescence.

Western blot analysis of PBGD: 50 mg of liver tissue were lysate using a radioimmunoprecipitation assay buffer (RIPA) (containing 150 mM NaCl, 250 mM Tris pH 7.7, 0.1% SDS, 0.5% sodium deoxycholate, 1% NP-40 and proteinase cocktail 1×). The tissue was homogenized for 30 sec each and incubated in an ice bath for 20 minutes. Afterward, the samples were centrifuged for 45 min at 16,000 g and 4° C. The supernatant was transferred to a new tube. The protein concentration was determined using Bradford method. 50 μg of protein was mixed 1:3 with sample buffer (containing 60 mM Tris pH 6.8, 10% glycerol, 2% SDS, 333 mM DTT and 0.01% Bromophenol Blue) and boiled 10 minutes at 95° C. for the denaturation of the proteins. 30 μL of the mixture was loaded on a denaturing gel 8% acrylamide. The proteins were transferred to a nitrocellulose membrane at 300 mA for 90 min at 4° C. The membrane was blocked (5% milk in Tris-buffered saline-Tween 20 0.1%) for 1 h. at RT, washed 3 times and incubated with goat anti-PBGD antibody (1:200) (SantaCruz Biotechnology) overnight at 4° C. Then, the membrane was washed again and incubated with HRP-labeled donkey anti-goat secondary antibody (1:10000) (R&D Systems) 1 h. at RT. The membrane was washed again with TBS-T 0.1% and the proteins were detected using a western lightening Plus ECL kit (Perkin Elmer) according to the manufacturer's instructions. Pre-stained protein standards with a molecular mass range 250-10 kDa were used (BioRad). As load control, proteins were revealed also after incubation with rabbit antiGAPDH antibody (1:1000) (Cell Signalling) and goat anti-rabbit secondary antibody (1:10000) (Sigma).

Statistical analysis: The non-parametric Mann-Whitney U-test was used for comparison of 2 different groups. In order to compare three or more groups, the Kruskal-Wallis test was performed. The null hypothesis was rejected when $p<0.05$. Statistical analyses were carried out with Graph Pad Prism v.5.

Results: When tested in the prokaryotic system, DNA plasmids encoding mutated variants $hkPBGD_{[I291M]}$ (abbreviated as PBGD-M), $hkPBGD_{[N340S]}$ (abbreviated as PBGD-S), $hkPBGD_{[H120Y]}$ (abbreviated as PBGD-Y), and $hkPBGD_{[S344N]}$ (abbreviated as PBGD-N) presented the higher increase in the enzymatic activity, although the PBGD-M and PBGD-S showed the largest increase (FIG. 1A) comparing to the control non-mutated human hkPBGD (abbreviated hPBGD).

FIG. 1 shows the change of certain amino acids in the PBGD sequence induces an increase in the catalytic activity of the enzyme. Human housekeeping PBGD enzyme was mutated in the positions I291M, N340S, H199Q, H120Y, S344N, Q332E, S45L or R164K generating the PBGD variants M, S, Q, Y, N, E, L, and K, respectively. The mutated PBGD sequences were compared to the human PBGD sequence in A) prokaryotic system and B) eukaryotic system. C) shows the synergic effect of the double mutation I291M and N340S in the catalytic capacity of the PBGD enzyme measured in a eukaryotic system. (D) Densitometry analysis of proteins on immunoblot assay from samples included in C) showed no significant differences between human and variant PBGD protein expression. The micrograph illustrated in E) is representative for immunochemical analysis of livers from animals expressing variant PBGD proteins. *, $p<0.05$; , $p<0.01$ *, $p<0.001$ vs control hPBGD plasmid.

Figure 1B:
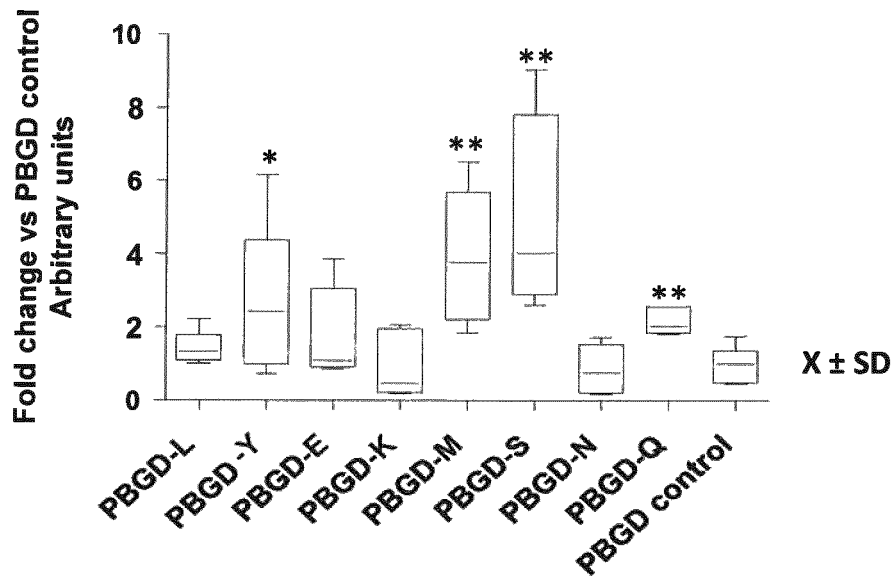
FIG. 1B is a graph showing the enzymatic fold changes of human housekeeping PBGD and various mutant variants when expressed in the liver of a mouse (eukaryotic system).

The increase in the activity changing these amino acids was also analyzed in the eukaryotic system as explained above. Measures of hepatic PBGD activities, normalized by the amount of plasmid DNA found into the liver samples, showed differences in the catalytic activity of the different PBGD mutants when just one amino acid of its sequence was modified (FIG. 1B). These results showed that the mutants of PBGD that presented the largest increase in its enzymatic activity were PBGD-S, PBGD-M, PBGD-Q and PBGD-Y. Although PBGD-S was the variant with the largest PBGD activity, which showed a PBGD activity of four-fold respect to the control PBGD.

Figure 1C:
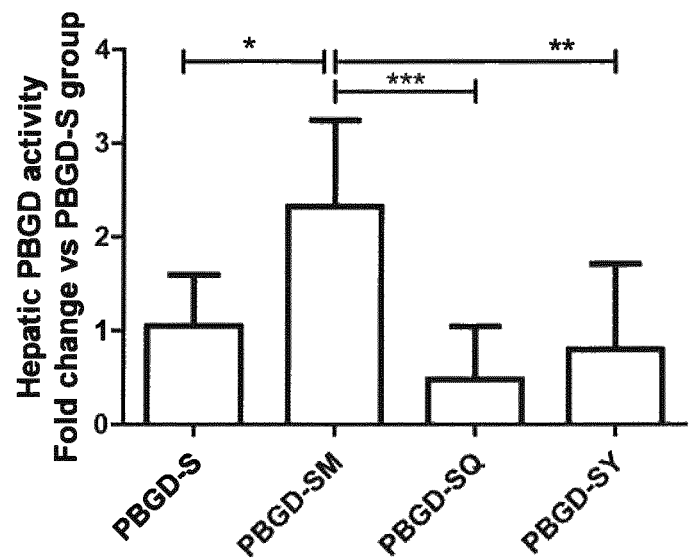
FIG. 1C is a graph showing the hepatic enzymatic activity of various PBGD mutant variants when expressed in the liver of a mouse (eukaryotic system).
Figure 1D:
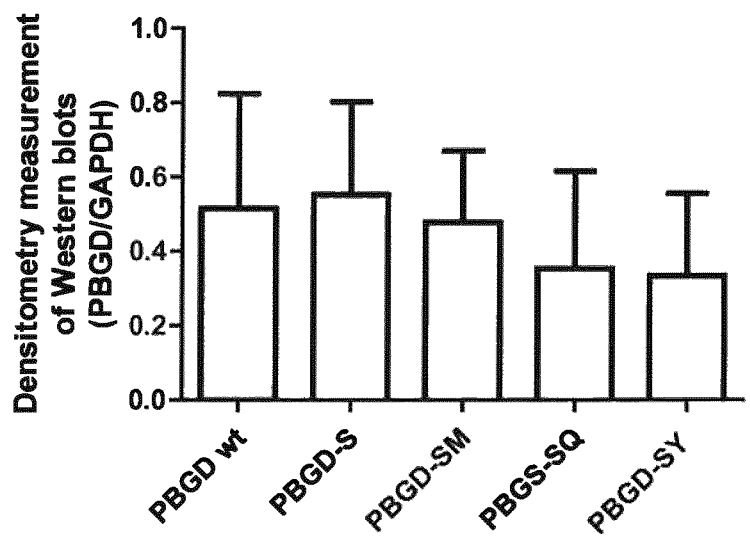
FIG. 1D is a graph showing the densitometry analysis of proteins on immunoblot assay from the samples included in FIG. 1C.
Figure 1E:
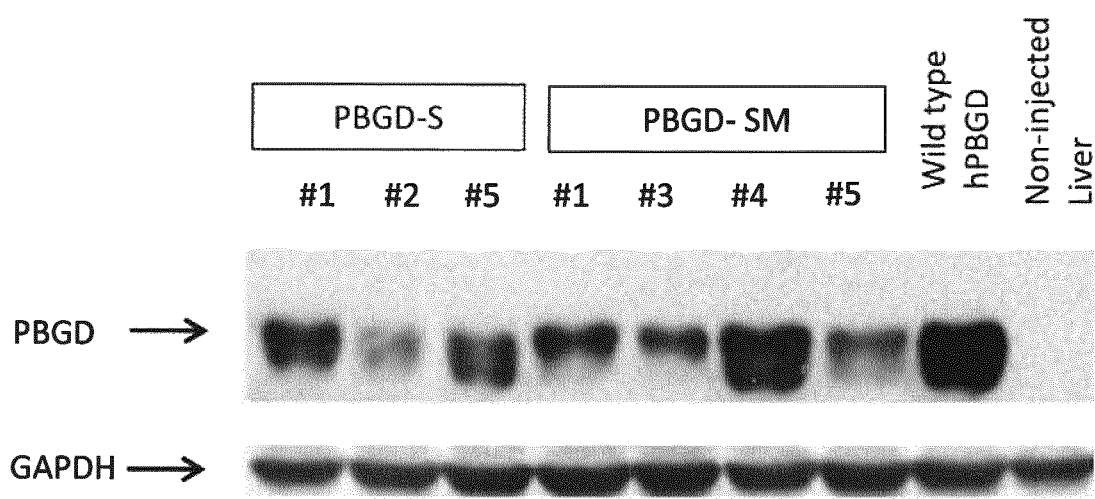
FIG. 1E is a photograph of a representative western blot comparing PBGD-S and PBGD-SM variants.

In order to identify if there was a synergic effect between the different amino acids mutations, new plasmid constructions were generated encoding mutant hkPBGD proteins incorporating modification that showed the largest increase in the PBGD activity (N340S), and additionally one of the other modifications (H120Y, I291M or H199Q). These plasmids were injected to four groups of mice by hydrodynamic injection and the increase in the hepatic PBGD activity was analyzed 24 hours later. As a control group, five AIP mice were injected plasmid encoding mutant hkPBGD$_{[N340S]}$ (PBGD-S). The FIG. 1C showed that the mutant hkPBGD$_{[N340S, I291M]}$ with the I291M and N340S modifications (abbreviated PBGD-SM) showed the largest increase of the enzymatic activity into the liver samples. This mutant showed a PBGD activity about 2 times higher than PBGD-S that had already shown a 4-fold higher activity than control human hkPBGD.

Afterward, extracted proteins from liver samples were analyzed by western blot to consider whether the increase in the enzymatic activity depended on the synthesized amount of protein or not (FIG. 1D). 50 μg of total protein were loaded on a denaturing gel and the western blot was revealed against the antibodies antiPBGD and antiGAPDH. Control hPBGD and PBGD-S, and PBGD-SM variants were expressed in equal quantity (FIGS. 1D and E) but PBGD-SM mutant was the one with the highest enzymatic activity (FIG. 1C).

Example 2. Therapeutic Efficacy of Viral Vector AAV2/8 Carrying as Transgene Sequence Encoding PBGD$_{[N340S, I291M]}$ The performance of AAV2/8-EalbAAT-PBGD vector, carrying codon optimized sequence encoding human hkPBGD, to prevent an acute attack in AIP mice was compared the therapeutic efficacy newly developed AAV2/8-EalbAAT-PBGD-Y and AAV2/8-EalbAAT-PBGD-SM vectors, which respectively carried codon optimized sequences encoding hkPBGD$_{[H120Y]}$, and hkPBGD$_{[N340S, I291M]}$ (SEQ.ID.NO.6).

Generation of AAV viral vectors: Single-stranded AAV2/8-EalbPAAT-PBGD, AAV2/8-EalbAAT-PBGD-Y and AAV2/8-EalbAAT-PBGD-SM vectors were produced for evaluation in AIP mouse model. Firstly, plasmids pro-AAV-PBGD constructs were generated by cloning expression cassettes of the vectors in a pro-AAV cloning vector (Berraondo P. et al. Mol. Ther. 2005; 12: 68-76; Maxwell F. et al. J. Virol. Methods 1997; 63:129-136). The expression cassette inserted in pro-AAV-PBGD had the polyA insulator sequence, the liver-specific promoter EalbAAT, the codon optimized synthetic sequence encoding human housekeeping PBGD or the PBGD variants and the 3'-UTR and polyadenylation sequences of human PBGD described by Unzu et al. (Mol Ther. 2011; 19: 243-250). Secondly, rAAV8 vectors with wild-type AAV2 ITRs were then produced in 293 T cells. For each production a mixture of plasmids, 20 μg of corresponding pro-AAV based plasmid and 55 μg of pDP8.ape (PlasmidFactory, KG, Bielefeld, Germany), was transfected into 293 T cells 15-cm plate using linear polyethyleneimine 25 kDa (Polysciences, Warrington, Pa.) as described (Durocher Y. et al., Nucleic Acids Res. 2002; 30:E9). The cells were harvested 48 hours after transfection and virus were released from the cells by three rounds of freeze-thawing. Crude lysate from all batches was centrifuged for 10 min at 4° C., 960 g, filtered (pore size, 0.45 μm) and further digested with 100 μg/ml DNase and RNase (both from Roche Diagnostic GmbH, Mannheim, Germany) for 30 min at 37° C. AAVs were purified from the supernatant by ultracentrifugation in Optiprep Density Gradient Medium-Iodixanol (Sigma-Aldrich, St Louis Mo.), following manufacturer instructions. The purified batches were then concentrated and diafiltrated by passage through Centricon tubes (YM-100; Millipore, Bedford, Mass.). After concentration, the viral batches were stored at −80° C. To titer the AAV productions, viral DNA was isolated using "The High Pure Viral Nucleic Acid" kit (Roche Applied Science. Mannheim, Germany). The concentration of viral particles was subsequently determined by real-time quantitative PCR using primers specific to for the PBGD polyadenylation sequence: pPBGDfw: 5'-gctagcctttgaatgtaacca-3' SEQ.ID.NO.18; and pPBGDrv: 5'-ccttcagaactggtttatt-agtagg-3', SEQ.ID.NO.19.

Murine AIP model: Compound heterozygote T1 (C57BL/6-pbgdtm1(neo)Uam) and T2 (C57BL/6-pbgdtm2(neo)Uam) strains described by Lindberg et al. [Nat. Genet. 1996, 12: 195-199] was used as a disease model for acute intermittent porphyria. These mice exhibit the typical biochemical characteristics of human porphyria, notably, a decreased hepatic PBGD activity and a massively increased urinary excretion of heme precursors in response to treatment with drugs such as phenobarbital. Porphyrins, mostly uroporphyrin (URO) and coproporphyrin are also elevated in AIP but increased urinary porphyrin is a much less specific feature than increases in porphobilinogen (PBG) and 5-aminolevulinic acid (ALA) levels.

Briefly, compound heterozygous AIP mice in C57BL/6 background of 12 to 25 weeks age were injected intravenously, via the tail vein, with a total volume of 200 μL of corresponding test substance (test viral vector). 44 mice were injected with different doses of test viral vectors AAV2/8-EalbAAT-PBGD (n=13), AAV2/8-EalbAAT-PBGD-Y (n=16) and AAV2/8-EalbAAT-PBGD-SM (n=15). The injected doses were respectively $1 \cdot 10^{11}$, $2 \cdot 10^{11}$, $3.3 \cdot 10^{11}$, $6.6 \cdot 10^{11}$, and $1 \cdot 10^{12}$ gene copies/kg (gc/kg).

To biochemically imitate a human porphyria attack; Two and six weeks post-treatment mice were intraperitoneally injected with two cycles of increasing doses of phenobarbital (75 mg/kg, 80 mg/kg, 85 mg/kg and 90 mg/kg body weight in four consecutive days), thus inducing two AIP attacks. After the last phenobarbital dose of each induction cycle, animals were housed during 24 h in metabolic cages (reference 3600M021 BIOSIS SL Biologic Systems) in order to collect 24 h-urine samples and to measure the accumulation of ALA and PBG.

Animals were sacrificed 24 h after the last dose of phenobarbital (54 days post-injection of test viral vector). Hepatic PBGD activity was analyzed as described in Example 1.

Determination of porphyrin and porphyrin precursors in urine samples: Care was taken to protect urine samples from light. Urinary excretion of δ-aminolevulinic acid (ALA) and porphobilinogen (PBG) were quantified using a quantitative ion exchange column method (BioSystems SA, Barcelona) and measured at 555 nm in an Ultrospec 3000 spectrophotometer (LS50B, PerkinElmer, Spain). Before porphyrin oxidation with Lugol's iodine solution, aliquots of 0.1 mL of 24 h-urine samples were dissolved in 1 mL of HCl 3N and with 3 mL of sodium thiosulfate to remove iodine stain. The concentration of porphyrins was determined by a spectrofluorometer (Perkin Elmer LS 50 B) with an excitation wavelength of 409 nm and the emission wavelengths of 550, 600 and 700 nm. Porphyrin levels were expressed in terms of nmol porphyrin/g creatinine.

Figure 2A:
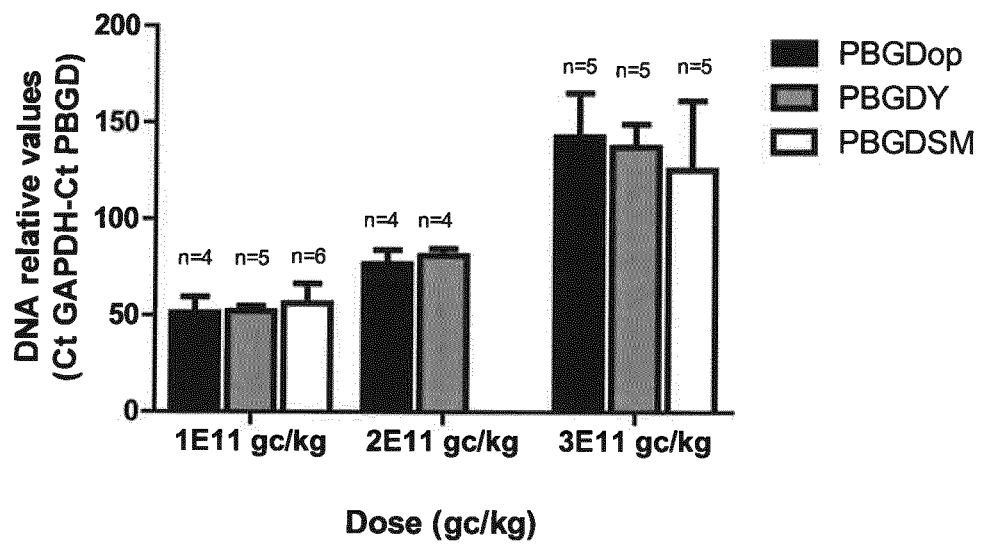
FIG. 2A is a graph showing vector DNA relative abundance in liver samples following administration of the same doses of the different vectors.

Results: The administration of the same doses of the different vectors showed a similar DNA concentration into the liver samples (FIG. 2A). Therefore, it was possible to compare the enzymatic PBGD activity generated by the administration of a specific viral vector and its therapeutic effect against an acute attack in mice injected with the same dose of different viral vectors.

Figure 2B:
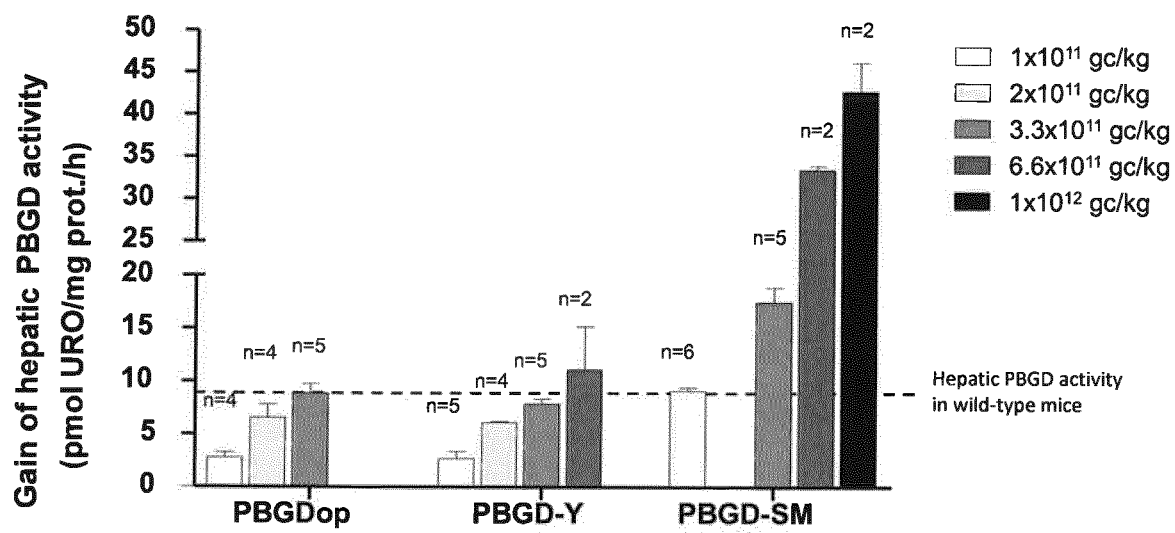
FIG. 2B is a graph showing a gain of hepatic PBGD activity in liver samples following administration of the same doses of the different vectors.

At the dose $1·10^{11}$ gc/kg, the gain of enzymatic activity in the liver samples was 3 times larger when mice were injected with AAV2/8-EalbAAT-PBGD-SM (FIG. 2B). The hepatic PBGD activity of a wild-type mouse is about 12 units, and an AIP mouse shows an enzymatic activity of about 3 units. Thus, the needed increase to normalize PBGD activity into the liver is about 9 units, which is the increase detected in the group of mice injected with the lowest dose of AAV2/8-EalbAAT-PBGD-SM. A dose 3 times higher of AAV2/8-EalbAAT-PBGD was required to obtain this same increase.

FIG. 2 shows the therapeutic efficacy of AAV2/8 vector carrying the variant PBGD-SM. Viral vectors PBGD-Y, PBGD-SM or non-mutated control PBGDop was injected to 4-5 mice per group. A) Control of the injected DNA in different doses of AAV. Vectors AAV2/8-EalbAAT-PBGD (abbreviated PBGDop), AAV2/8-EalbAAT-PBGD-Y (abbreviated PBGD-Y), and AAV2/8-EalbAAT-PBGD-SM (abbreviated PBGD-SM) were administered to 3 groups of mice (n=4-6) in different concentrations, $10^{11}$, $2·10^{11}$ and $3·10^{11}$ genomic copies per kg of mice. B) The lowest dose of the vector encoding PBGD-SM normalizes the PBGD activity to a wild type mouse. The injected doses for the PBGD-SM vector were $1·10^{11}$ gc/kg, $2·10^{11}$ gc/kg, $3.3·10^{11}$ gc/kg, $6.6·10^{11}$ gc/kg and $1·10^{12}$ gc/kg. Mice were sacrificed 54 days post-injection and its hepatic PBGD activity compared to groups of un-injected AIP and wild-type mice. Urinary C) PBG and D) ALA excretion measured at day 41 after the administration of AAV vector, just 24-hours after the last dose of phenobarbital. The dots showed the basal excretion of PBG. The administered doses were $1·10^{11}$, $2·10^{11}$ and $3·10^{11}$ gc/kg. (*, $p<0.05$; ***, $p<0.001$).

Figure 2C:
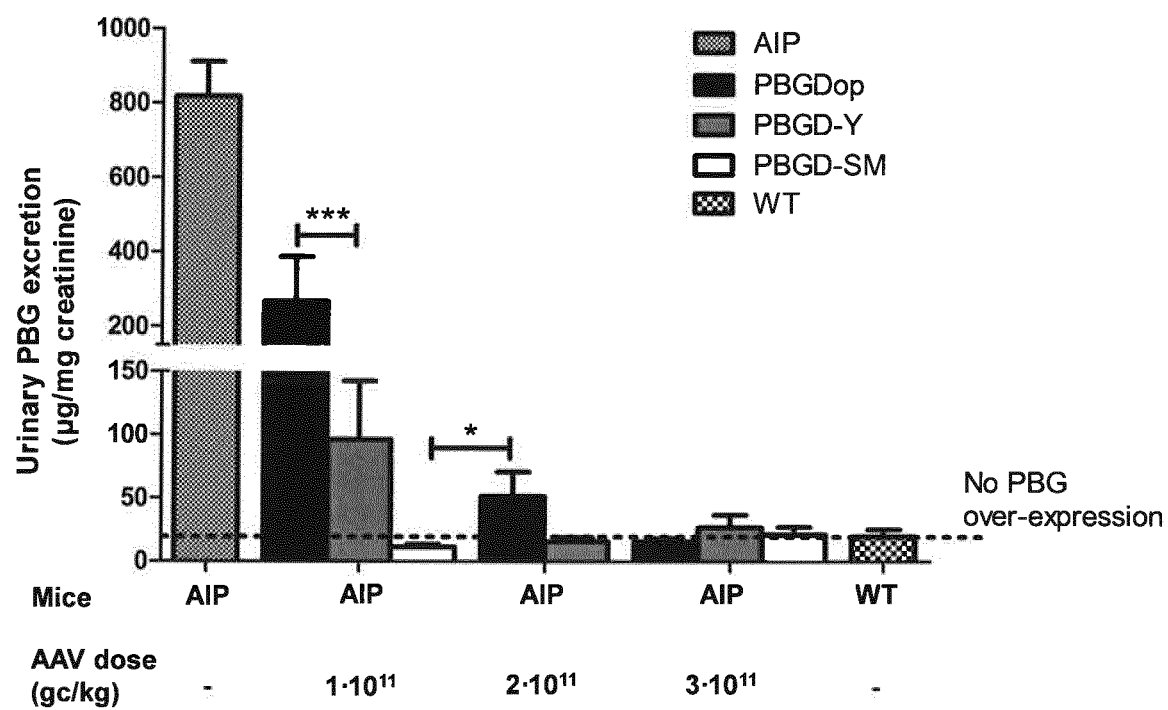
FIG. 2C is a graph showing urinary PBG excretion measured at day 41 after induction of an acute AIP attack with phenobarbital.
Figure 2D:
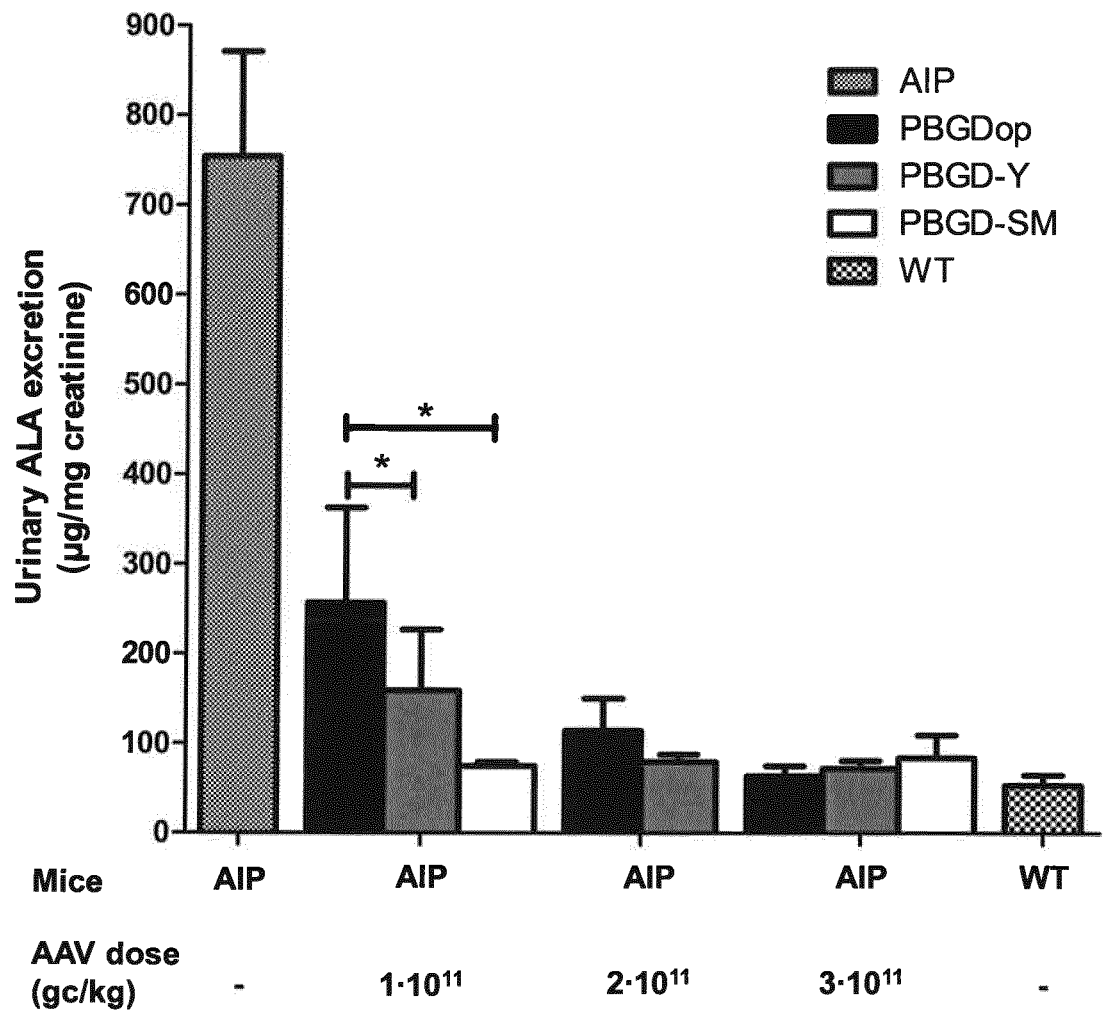
FIG. 2D is a graph showing urinary ALA excretion measured at day 41 after induction of an acute AIP attack with phenobarbital.

The inclusion of anew PBGD variant allows lowering three times the therapeutic dose of the AAV2/8-EalbAAT-PBGD. FIG. 2C and FIG. 2D showed the urinary excretion of PBG and ALA after the second induction of an acute attack with phenobarbital, respectively. Full protection against the phenobarbital-induced attack was obtained with $1·10^{11}$ gc/kg of the vector PBGD-SM. The protection offered by the injection of the same dose of vector PBGD-Y or non-mutated PBGDop was just partial.

AAV2/8-EalbAAT-PBGD-SM showed no accumulation of PBG or ALA when $1·10^{11}$ gc/kg were injected whereas AAV2/8-EalbAAT-PBGD needed $3·10^{11}$ gc/kg of vector to get the same therapeutic efficacy (FIG. 2C and FIG. 2D). Thus, the administration of PBGD-SM lowered 3 times the concentration required to have a therapeutic effect against a phenobarbital-induced attack in AIP mice.

Example 3. PBGD/Carrier Peptide Conjugate Compositions

The bioengineered housekeeping PBGD$_{[N340S, I291M]}$ variant (abbreviated as PBGDsm; SEQ.ID.NO.6) was fused to ApoAI (SEQ.ID.NO.7; as carrier polypeptide) to obtain two conjugate recombinant proteins differing in the relative position carrier and therapeutic protein (abbreviated as PBGDsm-ApoAI and ApoAI-PBGDsm). The proteins were produced by the company GenScript and its pharmacokinetics properties were compared with the corresponding conjugates of human housekeeping PBGD protein (SEQ.ID.NO.2) [PBGD-ApoAI; and ApoAI-PBGD]. In all four recombinant proteins, the PBGD form and carrier polypeptide were directly connected without introducing any connection linker.

Figure 3:
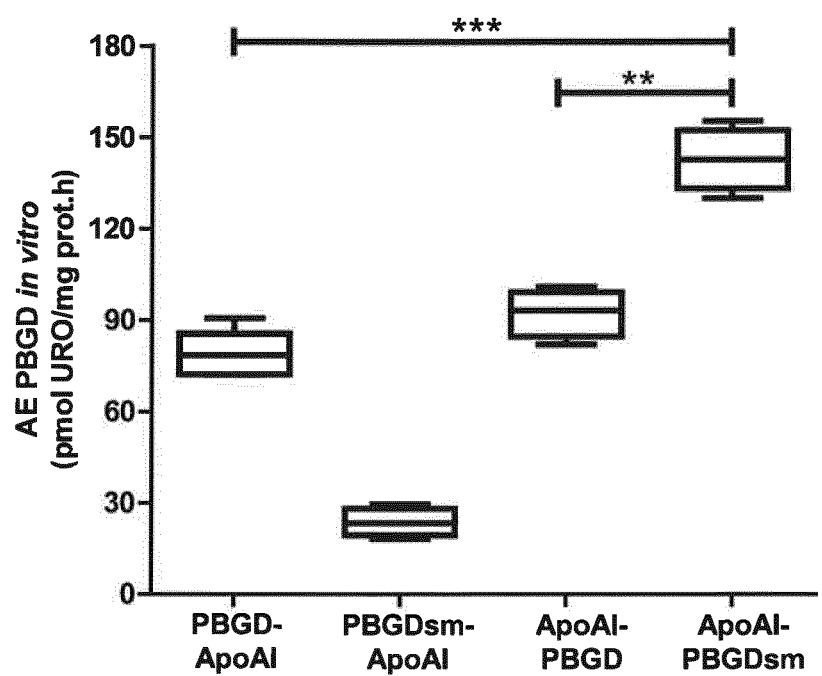
FIG. 3 is a graph showing the in vitro porphobilinogen deaminase activity produced by recombinant proteins PBGD-ApoAI, PBGDsm-ApoAI, ApoAI-PBGD, and ApoAI-PBGDsm.

The catalytic deaminase activity of the 4 conjugated proteins (PBGD-ApoAI, PBGDsm-ApoAI, ApoAI-PBGD, and ApoAI-PBGDsm) was quantified in vitro (FIG. 3).

FIG. 3 shows the in vitro porphobilinogen deaminase activity produced by recombinant proteins PBGD-ApoAI, PBGDsm-ApoAI, ApoAI-PBGD, and ApoAI-PBGDsm.

Equal amounts of each of the proteins (0.25, 0.5 and 1 μg) were incubated at 37° C. with porphobilinogen (PBG) substrate and then quantified the amount of formed URO by fluorescence. Proteins were previously quantified by an ELISA recognizing human ApoAI. (, $p<0.01$; *, $p<0.001$ vs reference housekeeping PBGD conjugated proteins).

The activity of ApoAI-PBGDsm protein significantly increased with respect to the activity of the ApoAI-PBGD conjugate protein (FIG. 3). However, the results show that the inverse arrangement, PBGDsm-ApoAI, significantly reduced the catalytic PBGD activity. The analysis of the quaternary structure of human PBGD protein suggests that the change in amino acids S and M gave rise to a more flexible dominium that could facilitate the entry of the first monopyrrole to the active center. However, the conjugation of the ApoAI to the carboxy terminus of PBGD (near where those mutations are located), abolished or even reduced this catalytic-potentiating effect.

ApoAI-PBGDsm then selected for further characterization tests. Permanence of the protein into the blood of mice injected with recombinant ApoAI-PBGDsm variant protein was determined. Control animals were respectively injected with: nonconjugated recombinant human housekeeping PBGD protein (rhPBGD), a conjugated protein PBGD-GAP-ApoAI, in which human housekeeping PBGD is connected to ApoAI by means of intercalating amino acids sequence GAP as linker connector, and a conjugated protein ApoAI-PBGD in which ApoAI and human housekeeping PBGD are directly connected without a linker connector (FIG. 4).

Figure 4:
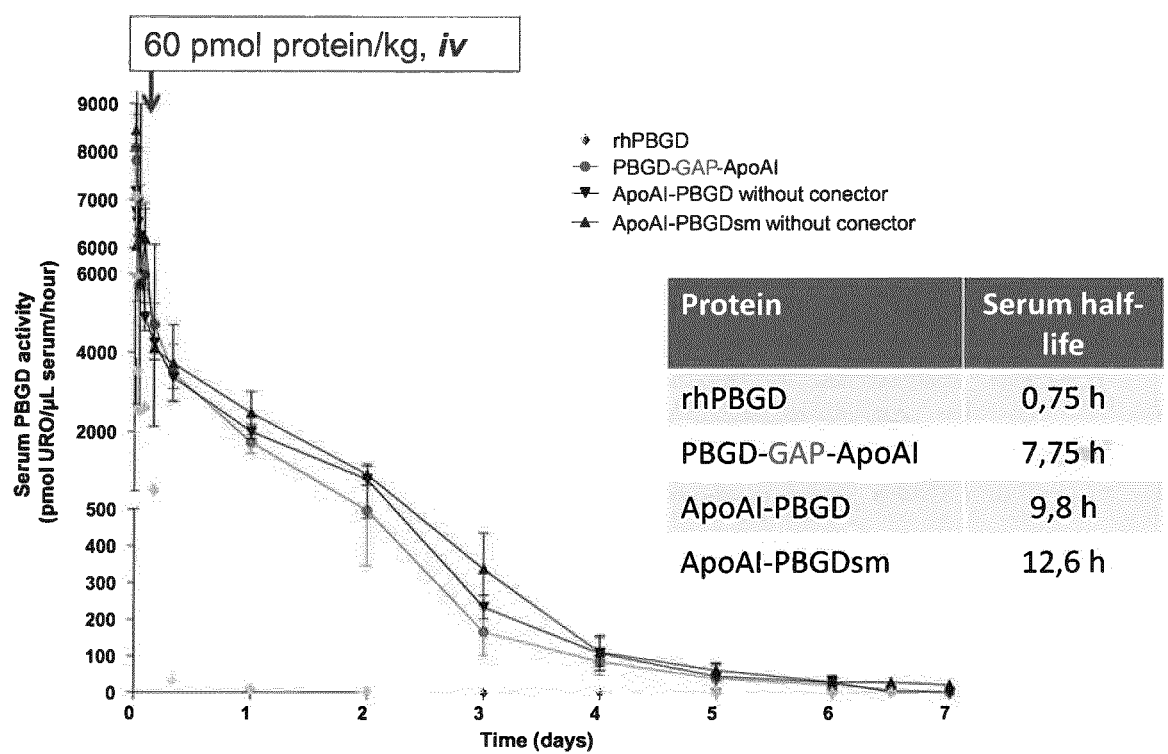
FIG. 4 is a graph showing the enzymatic porphobilinogen deaminase activity in serum during 7 days after the administration of a single dose of the recombinant protein.

FIG. 4 shows the enzymatic porphobilinogen deaminase activity in serum during 7 days after the administration of a single dose of the recombinant protein. To analyze their stability in serum, 4 groups of acute intermittent porphyria (AIP) mice (n=5) were injected with 60 pmol/kg of each of the recombinant proteins. Then, serum was extracted at different time points (5 min, 10 min, 20 min, 40 min, 60 min, 2 h, 4 h, 8 h, 24 h, 48 h, 3 d, 4 d, 5 d, 6 d and 7 d) to analyze the enzymatic activity and monitor the stability of each of the variants in serum. The results were shown as mean±SD.

The half-life of different recombinant proteins rhPBGD, PBGD-GAP-ApoAI, ApoAI-PBGD, and ApoAI-PBGDsm, was respectively 0.75 h, 7.75 h, 9.8 h, and 12.6 h (FIG. 4).

The PBGDsm variant fused with ApoAI at its amino-terminus showed increased serum stability which translates into increased half-life up to 12.6 hours. Since our reference parameter is the enzymatic activity, this data suggests that the stability of the protein is not modified but that enzymatic activity per unit of conjugated protein was greater with the ApoAI-PBGDsm variant.

Another great important advantage derived from the use of the ApoAI-PBGDsm variant could be the increase in the activity of hepatic PBGD. Thus, the same amount of conjugated protein targeting the liver will improve a greater enzymatic activity able to metabolize higher amounts of the PBG formed in the hepatocytes. To check this point, 300 pmol of each conjugated protein/kg (PBGD-ApoAI or ApoAI-PBGDsm) were injected into 2 groups of AIP mice. In another group, 60 pmol/kg of PBGD-ApoAI with chloroquine encapsulated in liposomes was also co-administered. At 24 hours after administration, mice were perfused to remove the circulating exogenous protein and the liver was removed to measure the PBGD activity (FIG. 5).

Figure 5:
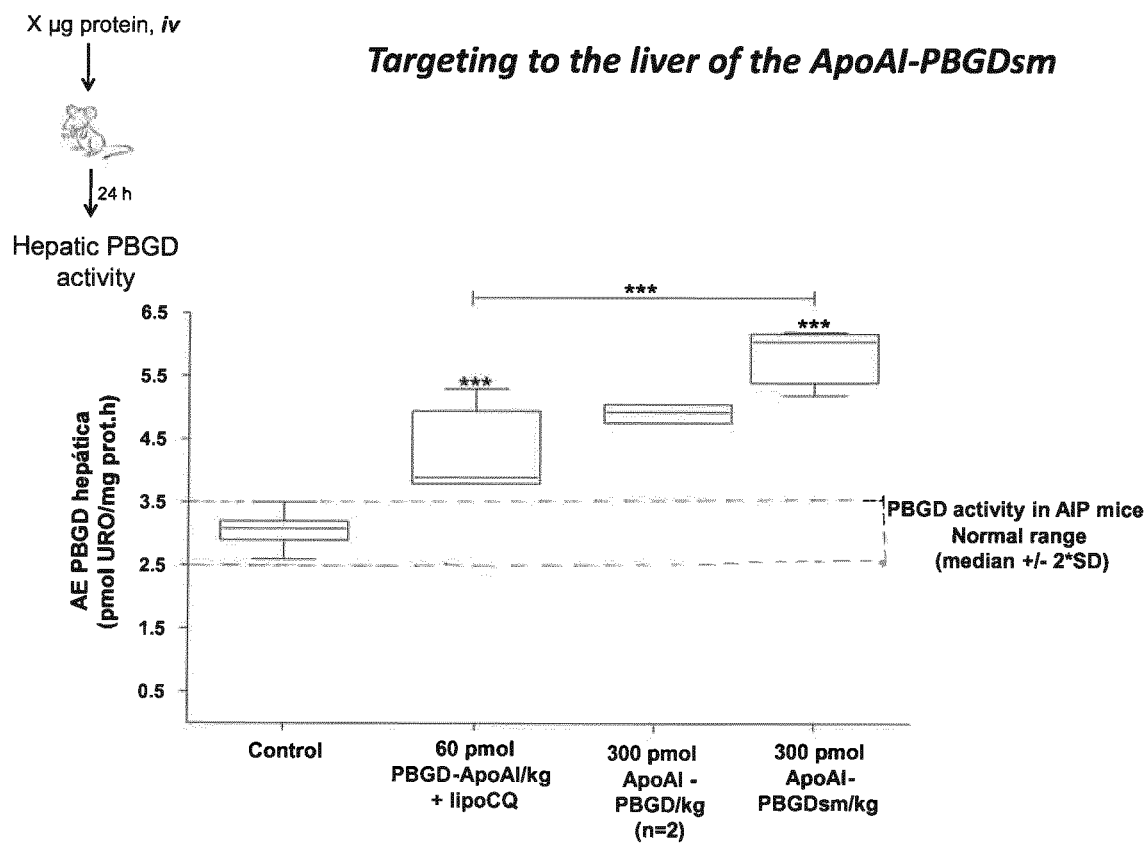
FIG. 5 is a graph showing that the intravenous administration of a high dose of ApoAI-PBGDsm variant increased in three units the activity of housekeeping PBGD in the liver of AIP mice.

FIG. 5 shows the intravenous administration of a high dose of ApoAI-PBGDsm variant increased in 3 Units the activity of housekeeping PBGD in the liver of AIP mice. 300 pmol of recombinant protein/kg (PBGD-ApoAI or ApoAI-PBGDsm) or the low dose of PBGD-ApoAI co-administered with chloroquine liposomes were administered to 3 groups of AIP mice. They were sacrificed at 24 hours, after hepatic perfusion with PBS, to analyze the entry of the functional PBGD protein in the hepatocyte. As a control, a group of uninjected mice was also analyzed. (***, p<0.001 vs control group). The gray band shows the normal range of PBGD activity in AIP mice.

As previously demonstrated, the co-administration of a mean dose of PBGD-ApoAI with chloroquine encapsulated in liposomes or the injection of a high dose of the same protein increased the hepatic activity of PBGD in AIP mice by 1 to 1.5 units (FIG. 5). Of interest, the administration of a high dose of ApoAI-PBGDsm increased the liver activity of PBGD by 3 units when compared to control liver AIP mice (FIG. 5). These data suggest that the conjugated PBGDsm variant may offer more efficient protection against acute porphyria attacks than conjugated natural human housekeeping PBGD proteins.

The increase of 1.5 units of PBGD activity in the liver (from 3 Units to 4.5 Units), obtained after the administration of high doses of PBGD-conjugated was sufficient to fully protects the accumulation of heme precursors induced after by phenobarbital challenge. In humans, liver samples collected from non-porphyrin volunteers showed a hepatic PBGD activity of 5.2±0.13 units, whereas liver explants from patients with acute intermittent porphyria showed an activity of 3.3±0.26 Units. Therefore, the increase of 3 units of activity would clearly normalize the hepatic activity of PBGD and will induce a long-lasting protection against the acute attacks in patients with AIP. Thus, the development of a PBGD variant with higher catalytic capacity would increase the therapeutic efficacy of the conjugated recombinant protein.

These results readily demonstrate that the conjugated ApoAI-PBGDsm variant protein exhibited significantly higher catalytic activity than the reference ApoAI-PBGD protein. This catalytic advantage is only observed when the carboxyl terminal end of the PBGD is free.

The invention claimed is:

1. A polypeptide comprising a) a human non-erythropoietic housekeeping porphobilinogen deaminase (PBGD) comprising at least one amino acid mutation with respect to SEQ ID NO:2 selected from the group consisting of mutations N340S, I291M, H199Q, H120Y, and S344N; or b) a human erythropoietic PBGD comprising at least one amino acid mutation with respect to SEQ ID NO:4 selected from the group consisting of mutations N323S, I274M, H182Q, H103Y, and S327N.

2. The polypeptide of claim 1, wherein the polypeptide comprises a) the human non-erythropoietic housekeeping PBGD comprising at least two amino acid mutations with respect to SEQ ID NO:2 selected from the group consisting of mutations N340S, I291M, H199Q, H120Y, and S344N; or b) the human erythropoietic PBGD comprising at least two amino acid mutations with respect to SEQ ID NO:4 selected from the group consisting of mutations N323S, I274M, H182Q, H103Y, and S327N.

3. The polypeptide of claim 1, wherein a) the human non-erythropoietic housekeeping PBGD comprising at least two amino acid mutations has increased deaminase activity when compared to the amino acid sequence of SEQ ID NO:2 or b) the human erythropoietic housekeeping PBGD comprising at least two amino acid mutations has increased deaminase activity when compared to the amino acid sequence of SEQ ID NO:4.

4. The polypeptide of claim 2, wherein the human non-erythropoietic housekeeping PBGD comprises amino acid mutations N340S and I291M with respect to SEQ ID NO:2.

5. The polypeptide of claim 4, wherein the polypeptide has the amino acid sequence of SEQ ID NO:6.

6. A polynucleotide or nucleic acid construct comprising a nucleic acid sequence encoding the polypeptide of claim 1.

7. The polynucleotide or nucleic acid construct of claim 6, wherein the polynucleotide or nucleic acid construct has the nucleic acid sequence of SEQ ID NO:5.

8. A vector comprising the polynucleotide or nucleic acid construct of claim 6.

9. A host cell comprising the polypeptide of claim 1.

10. A pharmaceutical composition comprising the polypeptide of claim 1, and a pharmaceutically acceptable carrier or excipient.

11. A method for treating, or ameliorating at least one symptom of, a condition associated with, or caused by, a deficiency in porphobilinogen deaminase in a subject in need thereof comprising administering to said subject a therapeutically effective amount of the polypeptide of claim 1.

12. The method of claim 11, wherein the deficiency in porphobilinogen deaminase is acute porphyria.

13. The method of claim 11, wherein the deficiency in porphobilinogen deaminase is acute intermittent porphyria.

14. A method for increasing porphobilinogen deaminase activity in a subject in need thereof comprising administering to said subject a therapeutically effective amount of the polypeptide of claim 1.

15. A composition comprising: (i) an Apo A protein, or a functionally equivalent variant thereof, and (ii) the polypeptide of claim 1.

16. The composition of claim 15, wherein components (i) and (ii) are covalently bound and wherein components (i) and (ii) form a single polypeptide chain.

17. The composition of claim 15, wherein the Apo A protein is selected from the group of ApoA-I, ApoA-II, ApoA-IV, and ApoA-V, or a functionally equivalent variant thereof.

18. The composition of claim 15, wherein the Apo A protein is human ApoA-I.

19. The composition of claim 18, wherein the human ApoA-I protein has the amino acid sequence of SEQ ID NO:7.

20. The composition of claim 15, wherein the C-terminal end of component (i) is bound to the N-terminal end of component (ii) or wherein the N-terminal end of component (i) is bound to the C-terminal end of component (ii).

21. The composition of claim 20, wherein the C-terminal end of component (i) is bound to the N-terminal end of component (ii).

22. The composition of claim 15, wherein the composition comprises the amino acid sequence of SEQ ID NO:13.

23. A polynucleotide or nucleic acid construct comprising a nucleic acid sequence encoding the composition of claim 15.

24. The polynucleotide or nucleic acid construct of claim 23, wherein the polynucleotide or nucleic acid construct has the nucleic acid sequence of SEQ ID NO:12.

25. A vector comprising the polynucleotide or nucleic acid construct of claim 23.

26. A host cell comprising the composition of claim 15.

27. A pharmaceutical composition comprising the composition of claim 15, and a pharmaceutically acceptable carrier or excipient.

28. A method for treating, or ameliorating at least one symptom of, a condition associated with, or caused by, a deficiency in porphobilinogen deaminase in a subject in need thereof comprising administering to said subject a therapeutically effective amount of the composition of claim 15.

29. The method of claim 28, wherein the deficiency in porphobilinogen deaminase is acute porphyria.

30. The method of claim 28, wherein the deficiency in porphobilinogen deaminase is acute intermittent porphyria.

31. A method for increasing porphobilinogen deaminase activity in a subject in need thereof comprising administering to said subject a therapeutically effective amount of the composition of claim 15.

* * * * *